(12) United States Patent
Alecu et al.

(10) Patent No.: US 9,390,160 B2
(45) Date of Patent: Jul. 12, 2016

(54) SYSTEMS AND METHODS FOR PROVIDING IMPROVED ACCESS TO PHARMACOVIGILANCE DATA

(75) Inventors: Iulian Alecu, Paris (FR); Cedric Bousquet, Paris (FR); Marie-Christine Jaulent, Vanves (FR)

(73) Assignee: CEDRIC BOUSQUET, Lyons (FR)

( * ) Notice: Subject to any disclaimer, the term of this patent is extended or adjusted under 35 U.S.C. 154(b) by 1423 days.

(21) Appl. No.: 11/843,394

(22) Filed: Aug. 22, 2007

(65) Prior Publication Data

US 2009/0055378 A1 Feb. 26, 2009

(51) Int. Cl.
| | | |
|---|---|---|
| G06F 17/30 | (2006.01) | |
| G06F 19/00 | (2011.01) | |
| G06Q 10/00 | (2012.01) | |
| G06Q 50/22 | (2012.01) | |

(52) U.S. Cl.
CPC ........ G06F 17/30616 (2013.01); G06F 19/326 (2013.01); G06Q 10/00 (2013.01); G06Q 50/22 (2013.01); *G06F 19/324* (2013.01); *G06F 19/3406* (2013.01)

(58) Field of Classification Search
CPC ............ G06F 19/3456; Y10S 707/923; Y10S 707/941; Y10S 707/944; Y10S 707/99945; Y10S 707/99948
USPC ........... 707/999.101–999.102, 705, 756, 805; 705/3
See application file for complete search history.

(56) References Cited

U.S. PATENT DOCUMENTS

| | | | |
|---|---|---|---|
| 6,507,829 B1 * | 1/2003 | Richards et al. ................ 706/45 |
| 6,684,221 B1 * | 1/2004 | Rejndrup ................... 707/104.1 |
| 6,952,695 B1 * | 10/2005 | Trinks et al. |
| 7,363,305 B2 * | 4/2008 | Gabbert et al. ................... 707/8 |
| 2002/0165853 A1 * | 11/2002 | Gogolak ........................... 707/3 |
| 2002/0188465 A1 * | 12/2002 | Gogolak ........... G06F 17/30595 705/2 |
| 2003/0163488 A1 * | 8/2003 | Kloos et al. ................... 707/200 |
| 2004/0049522 A1 * | 3/2004 | Streepy, Jr. ................ 707/104.1 |
| 2005/0027566 A1 * | 2/2005 | Haskell ............................. 705/2 |
| 2005/0091081 A1 * | 4/2005 | Park ........................ G06Q 50/22 705/2 |
| 2006/0111847 A1 * | 5/2006 | Pearson et al. ................... 702/19 |
| 2007/0005621 A1 * | 1/2007 | Lesh et al. ..................... 707/101 |
| 2007/0067184 A1 * | 3/2007 | Harp et al. ......................... 705/2 |
| 2007/0067279 A1 * | 3/2007 | Bonabeau ......... G06F 17/30864 |
| 2007/0143273 A1 * | 6/2007 | Knaus et al. ....................... 707/3 |

OTHER PUBLICATIONS

Unified Medical Language System Fact Sheet. Last updated Mar. 23, 2006. http://www.nlm.nih.gov/pubs/factsheets/umls.html.*

(Continued)

*Primary Examiner* — Miranda Huang
(74) *Attorney, Agent, or Firm* — Hunton & Williams LLP

(57) ABSTRACT

A system and method for browsing a pharmacovigilance database with a graphical representation that shows relationships between medical terms may include providing access to a plurality of medical terminologies and mapping medical terms of the plurality of terminologies to a searchable database by using a semantic network to relate the medical terms of the different terminologies. The system and method may further include providing a graphical user interface that enables graphical navigation of the plurality of terminologies, enables display of a mapping between a first medical term from a first medical terminology to a second medical term from a second medical terminology, and enables coding of pharmacovigilance reports using medical terms of the second terminology based on a description provided using medical terms of the first terminology.

20 Claims, 20 Drawing Sheets

(56) References Cited

OTHER PUBLICATIONS

Y. Lee et al., Computers in Biology and Medicine 36, 2006 pp. 893-919.*

Hasman et al., Ubiqllity: Teclmologit!sfor Beller Health jll Aging Societies, IOS Press, Aug. 2006, pp. 833-838, Mapping of the Who-Art terminology on Snomed CT to improve grouping of related adverse drug reactions.*

* cited by examiner

Do a substring search (wildcards allowed):
hemorrhage                              [Find string]
Search within:
WHO-ART (W) ☐
MedDRA (M) ☐
Snomed-CT (S) ☑

Free text search result for:

hemorrhage
Number of matches = 80
S:Subarachnoid_hemorrhage_NOS()
S:Subarachnoid_hemorrhage()
S:Hemorrhage_at_vitreoretinal_interface()
S:Intraocular_hemorrhage()
S:Brain_stem_hemorrhage()
S:Intracerebral_hemorrhage()
S:Gastrointestinal_hemorrhage_unspecified()
S:Gastrointestinal_tract_hemorrhage_NOS()
S:Hemorrhage()
S:Intracranial_hemorrhage_NOS()
S:Intracranial_hemorrhage()
S:Subdural_hemorrhage()
S:Hemorrhage_of_blood_vessel()
S:Melena_due_to_gastrointestinal_hemorrhage()
S:Neonatal_cerebral_hemorrhage()
S:Cerebral_hemorrhage()
S:Perinatal_intracranial_hemorrhage()
S:Cerebral_hemorrhage_in_fetus_OR_newborn()
S:Unspecified_gastric_ulcer_with_hemorrhage()
S:Hemorrhage_of_muscle()
S:Splinter_hemorrhage()
S:Vitreous_hemorrhage()
S:Upper_gastrointestinal_hemorrhage()
S:Subdural_hemorrhage_NOS()
S:Hemorrhage_of_liver()

⟵ 706

[Clear Query] [Restrict] [Enlarge] [Clear Restrict]
   810       812       814        816

WHO-ART concepts related to:

Stomach_structure AND *Hemorrhage* ⟵ 806

[Graphic navigation] ⟵ 808

Number of matches = 21
W:GASTRITIS_HAEMORRHAGIC(PT)
W:GASTRITIS_HAEMORRHAGIC_AGGRAVATED(PT)
W:GASTRITIS_EROSIVE(HLT)
W:PERFORATION_AND_HAEM_GAST_ULCER(PT)
W:GASTRIC_ULCER_HAEMORRHAGIC(PT)
W:GASTRIC_ULCER_HAEMPER(PT)
W:STOOL_TARRY(PT)
W:MELAENA(PT)
W:OESOPHAGEAL_HAEMORRHAGE(PT)
W:BLOOD_PER_RECTUM(PT)
W:RECTAL_BLEEDING(PT)
W:HAEMATEMESIS(PT)
W:FAECES_BLOODSTAINED(PT)
W:ANAL_HAEMORRHAGE(PT)
W:HAEMORRHAGE_RECTUM(PT)
W:BLOOD_IN_STOOL(PT)
W:STOOL_BLACK(PT)
W:FAECAL_OCCULT_BLOOD_POSITIVE(PT)
W:VOMITING_BLOOD(PT)
W:HAEMORRHAGE_GASTRIC(HLT)
W:MALLORY_WEISS_SYNDROME(PT)

⟶ 804

[Go to detailed PhV cases] ⟵ 820

Pharmacovigilance Report Searching
           822

Build Customized Set of Terms
           824

FIG. 8

SYSTEMS AND METHODS FOR PROVIDING IMPROVED ACCESS TO PHARMACOVIGILANCE DATA

BACKGROUND INFORMATION

Using drugs safely is an international public health issue. Adverse drug reactions constitute one of the ten principal causes of mortality in the United States. In France, one hospitalization out of ten is the consequence of an adverse drug reaction.

According to the World Health Organization (WHO), pharmacovigilance is "the science and activities relating to the detection, assessment, understanding and prevention of adverse effects or any other drug-related problem." Pharmacovigilance is the medical domain related to the review, statistical analysis, and detection of adverse reactions related to drug administration. The purpose of pharmacovigilance is to identify a potential relationship between a drug and an adverse reaction, defined as a clinical manifestation unexplained by the natural evolution of the patient clinical condition. The adverse reaction status is justified only by the logical exclusion of any other factors related to the patient, hence allowing the intake drug to be incriminated. These hypotheses must be justified by conducting research to establish a causality relationship between the drug and the adverse reaction.

Pharmacovigilance reports describe and code observations of adverse reactions after drug administration. Pharmacovigilance reports also may be referred to as drug safety reports. Pharmacovigilance reports describe the suspicion of a causal relation between the administered drugs and the observed reactions. These reports are centralized and stored in national and international databases, and are periodically manually reviewed by medical experts. Some statistical scans can be done on these databases to attempt to detect or to confirm a problem related to a particular drug. These databases are very large, for example, there are 3.8 million reports in the World Health Organization international database. Moreover, the number of pharmacovigilance reports related to adverse drug reactions is exponentially increasing. Therefore, detecting a medical problem in such databases can be very difficult as adverse reactions are often rare events.

The rapid and effective review of pharmacovigilance reports involves: 1) Accurate coding and documenting of pharmacovigilance reports based on the World Health Organization—Adverse Reaction Terminology (WHO-ART) and Medical Dictionary for Drug Regulatory Activities (MedDRA) regulatory coding terminology, and 2) Efficient grouping of similar pharmacovigilance reports through the terminology structure (i.e., hierarchy). The coding terminology has an important role in indexing, sharing, analysis, and reporting of data during clinical trials and for post marketing drug surveillance.

Pharmacovigilance case assessment, however, is a highly costly task within drug safety departments. In the last few years, the focus on drug safety terminology has increasingly shifted from coding to data retrieval and analysis for risk assessment and safety signal detection (e.g., data mining).

The terminologies currently being used for pharmacovigilance report coding are not optimal for data retrieval and case review. Indeed, these terminologies do not group pharmacovigilance reports to enable a user to efficiently review specific medical issues, particularly those medical issues not covered by the requirements of the regulatory authorities.

The computational representation of terminologies for pharmacovigilance is difficult. Most items in a pharmacovigilance report are described using medical terms. Physicians can naturally understand the meaning of terms and exchange this meaning with colleagues due to their knowledge of medicine. When information is transferred from the paper-based description of an adverse drug reaction to a pharmacovigilance database, the meaning of information may be lost in different computational operations. If data about the patient and knowledge about the adverse drug reaction can be represented, the computer system can accomplish many tasks that may enhance the ability to retrieve relevant pharmacovigilance cases and learn more about adverse drug reactions. One approach to such representation is knowledge representation, a collection of techniques drawn from computer science.

A concept is an abstract, universal psychical entity that serves to designate a category or class of entities, events, or relations. A concept as a "unit of thought" may include two parts: 1) its extension, which includes all objects belonging to the concept, and 2) its intension, which includes all attributes belonging to the concept. In knowledge based systems, these concepts are described using a formal language. A formal language is a language that can be processed by a computer to produce results which meaning can be understood by the user.

Three generations of terminologies have been used to provide concept representation systems in medicine.

First generation terminologies are based on textual descriptions of concepts. These terminologies do not provide categorical structure, and concepts are designated by codes and strings. These traditional terminologies are paper-based, but can be electronically available to allow the storage, transmission, and retrieval of strings and codes attached to the concepts. These types of terminologies have a fixed and usually unique hierarchy devoted to a single application.

An example of a first generation terminology is World Health Organization—Adverse Reaction Terminology (WHO-ART), which may be used in pharmacovigilance for data coding and data statistical analysis. WHO-ART was the first adverse event terminology used in pharmacovigilance and was created in 1968 by the founders of international pharmacovigilance system. The WHO-ART system is maintained by the Uppsala Monitoring Centre, which is the World Health Organization's collaborating center for international drug monitoring. WHO-ART is a dictionary meant to serve as a basis for rational coding of adverse drug reaction terms. The main purpose of WHO-ART was to give a standardized way to input data in early computer databases. WHO-ART terminology has been developed for more than 30 years and serves as a basis for rational coding of adverse reaction terms. WHO-ART terminology has a hierarchical structure with restricted multiple inheritance. WHO-ART has three levels in theory, but is primarily organized in only two levels and medical terms with different levels of generalization may be siblings.

WHO-ART is organized on three hierarchical levels: (1) adverse drug reactions (ADRs) are coded using one thousand eight hundred and fifty seven preferred terms (PT); (2) some PTs are grouped into one of one hundred and eighty high level term (HLT) classes; and, (3) at the most general level, PTs are grouped according to thirty two system organ classes (SOC). Most SOCs group terms according to an anatomical perspective, for example, in a "Gastrointestinal disorders" SOC, and some of the SOCs use a problem oriented approach to group terms, for example, in a "Neoplasm" SOC.

MedDRA is another example of a first generation terminology. MedDRA defines a clinically validated international medical terminology used by regulatory authorities and the regulated biopharmaceutical industry throughout the entire regulatory process (from pre-marketing to post-marketing activities) for data entry, retrieval, evaluation, and presentation. In addition, MedDRA provides the adverse event classification dictionary endorsed by the International Conference on Harmonization of Technical Requirements of Pharmaceuticals for Human use. MedDRA is used in the United States, European Union, and Japan, with its use currently mandated in Europe and Japan for safety reporting.

MedDRA coding terminology is hierarchical and multi-axial in nature. A data retrieval section of MedDRA is an associative grouping of terms. The different levels of the terminology in MedDRA from highest (broadest concept) to lowest (most specific) are the following: (1) System Organ Class (SOC); (2) High Level Group Term (HLGT); (3) High Level Term (HLT); (4) Preferred Term (PT); and (5) Lowest Level Term (LLT). MedDRA has similar organization as WHO-ART, with one difference being that MedDRA includes a new level of grouping HLGT, thus allowing MedDRA to include a greater number of groupings than WHO-ART.

Second generation terminologies are compositional systems which are built using a categorical structure and a cross thesaurus. The categorical structure is composed of a set of meta-term descriptors to describe a concept in a domain of expertise. For example, <morphology>, <function>, <topography>, and <etiology> are useful descriptors for the categorical structure of adverse drug reactions. A morphology descriptor may contain terms used to describe structural changes in the body. An example of a morphology is "inflammation." A function descriptor may contain terms used to describe both normal and abnormal functions of the body. An example of a function is "tachycardia." A topography descriptor may contain detailed anatomic terms. An example of a topography is "upper limb." An etiology descriptor may contain terms that deal with the causes or origin of disease, and the factors which produce or predispose toward a certain disease or disorder. The etiology descriptor may include, for example, living agents such as, bacteria, viruses, or parasites.

A term from a first generation system (e.g., WHO-ART, MedDRA) may benefit from a description using a second generation terminology. For example, the MedDRA term "Gastric ulcer hemorrhage," which is an example of a "molecular" terminology phrase, may be dissected into basic units. Terms that cannot be further dissected are "atomic" terms, e.g., ulcer, stomach, hemorrhage. The cross thesaurus is a multiaxial thesaurus that provides the atomic terms to enter descriptors from the categorical structure. For example, a Gastric ulcer hemorrhage could be described by the following dissection:

Gastric ulcer hemorrhage is an adverse drug reaction that:
has_morphology: hemorrhage AND ulcer
has_finding_site: stomach
Relationships such as "has_morphology" and "has_finding_site" are semantic links.

In third generation terminologies, terms are described using a logical language and the position of terms in the hierarchy is found by computing subsumption relations. For example, "gastric ulcer hemorrhage" is a kind of "gastric ulcer." In this setting, a concept is defined by a label and a formal definition. The formal definition is composed by a number of phrases expressed according to a logical formal language aiming to indicate one and only one meaning to the label (i.e., disambiguate) from the various signification that one person could give.

An example of a third generation terminology is Systematized Nomenclature of Medicine-Clinical Terms (SNOMED CT). SNOMED CT is a systematically organized computer processable collection of medical terminology covering most areas of clinical information, such as diseases, findings, procedures, microorganisms, pharmaceuticals, etc. SNOMED CT allows a consistent way to index, store, retrieve, and aggregate clinical data across specialties and sites of care. SNOMED CT also helps organize the content of medical records, reducing the variability in the way data is captured, encoded, and used for clinical care of patients and research. The design of SNOMED CT is based on "description logic."

SNOMED CT is emerging as a standard terminology for data coding in clinical domains. SNOMED CT may be used to represent signs, symptoms, diseases, and laboratory examination results. SNOMED CT is an attempt to provide a formal ontology in the medical field. An ontology is a formal system whose purpose is to represent knowledge in a specific domain by means of basic elements called concepts, which are defined and organized in relation to the one another.

Conventionally, pharmacovigilance reports stored in pharmacovigilance databases are typically accessed using a lexical search (i.e., search by character string, key words, and synonyms) or by navigation within the groupings of the terminologies (e.g., WHO-ART, MedDRA) used for the coding. This approach is problematic due to organizational problems of the WHO-ART and MedDRA terminologies. In particular, grouping of preferred terms (PT) by means of high level terms (HLT) is not always carried out in a systematic and consistent way.

For example, WHO-ART is a mix of diagnostic and descriptive terms. Often pharmacovigilance reports confusingly contain a combination of diagnostic and descriptive terms as a descriptive part of a disease that can also be covered by a diagnostic term. The hierarchical organization of WHO-ART also may lead to characteristic details that are hidden behind higher level terms and may split up a general pattern over different low level terms (i.e., descriptive terms). This is aggravated by some inconsistencies in WHO-ART (e.g., myocardial infarction and thrombosis coronary were two different terms in different SOCs without any link).

A problem with the MedDRA terminology is that MedDRA terms can be linked to only one HLT inside the same SOC. For example, "gastric ulcer hemorrhage" belongs to the "gastric ulcer and perforations" HLT, but not to the "gastric and esophageal hemorrhage" HLT. Therefore, there is a missing relationship between the "gastric ulcer hemorrhage" PT and the "gastric and esophageal hemorrhage" HLGT due to the structural design of MedDRA. In another example, the "gastric ulcer and perforations" HLT is linked to the "vascular hemorrhagic disorder" HLGT in the "vascular disorder" SOC. This may help the user to find additional gastric hemorrhages, but the "vascular hemorrhagic disorder" HLGT may contain other hemorrhages that are not located in the stomach.

These and other problems exist with conventional systems.

BRIEF DESCRIPTION OF THE DRAWINGS

Purposes and advantages of the exemplary embodiments will be apparent to those of ordinary skill in the art from the following detailed description in conjunction with the appended drawings in which like reference characters are used to indicate like elements, and in which:

FIG. 8 illustrates a PharmARTS graphical user interface after a user has selected a defining term in accordance with exemplary embodiments;

Figure 1:
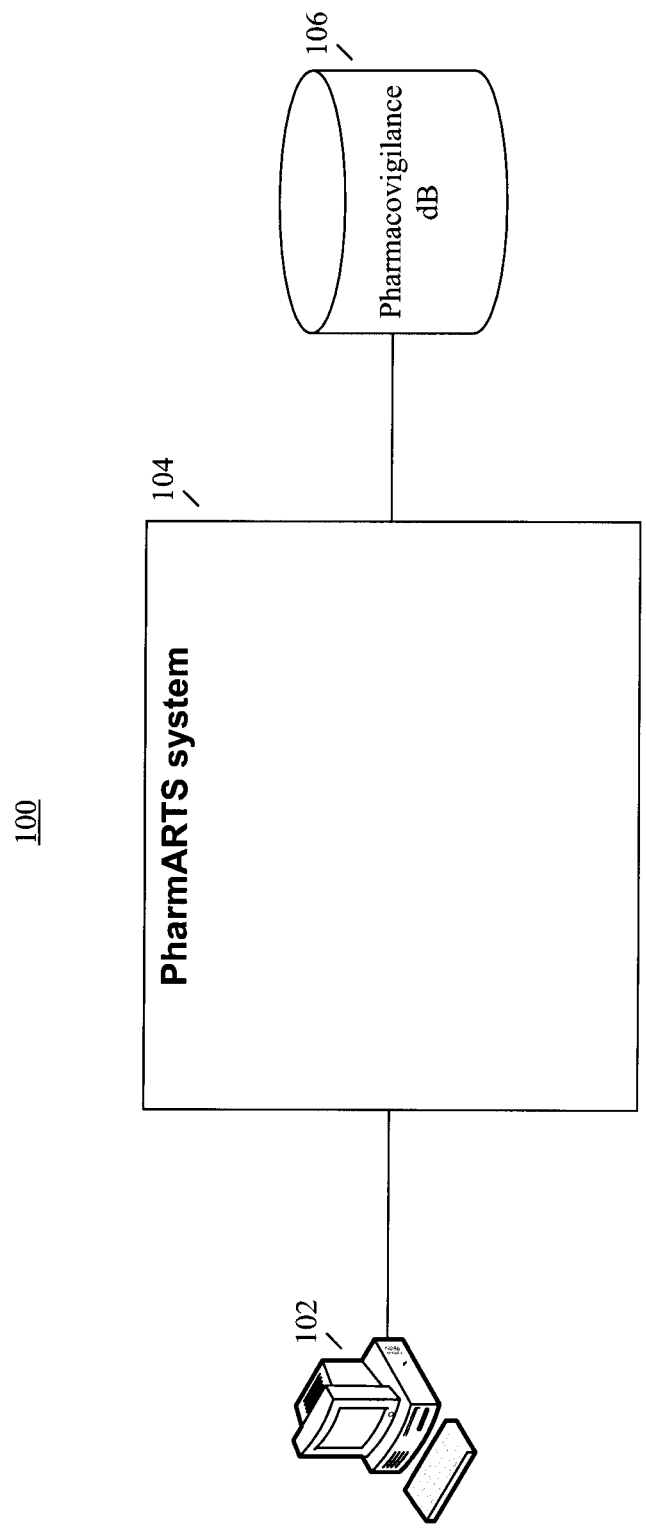
FIG. 1 illustrates a system in accordance with exemplary embodiments.

These and other embodiments and advantages will become apparent from the following detailed description, taken in conjunction with the accompanying drawings, illustrating by way of example the principles of the various exemplary embodiments.

SUMMARY OF THE INVENTION

A method for browsing a pharmacovigilance database with a graphical representation that shows relationships between medical terms in accordance with exemplary embodiments may include providing access to a plurality of medical terminologies, and mapping medical terms of the plurality of terminologies to a searchable database by using a semantic network to relate the medical terms of the different terminologies. The method may further include providing a graphical user interface that enables graphical navigation of the plurality of terminologies, enables display of a mapping between a first medical term from a first medical terminology to a second medical term from a second medical terminology, and enables coding of pharmacovigilance reports using medical terms of the second terminology based on a description provided using medical terms of the first terminology.

A system for browsing a pharmacovigilance database with a graphical representation that shows relationships between medical terms in accordance with exemplary embodiments may include a resource comprising a plurality of medical terminologies and a semantic network that expresses relations between medical terms of the medical terminologies. The system may further include a terminology server that maps the medical terms of the plurality of medical terminologies to a searchable database by using the semantic network to relate the medical terms of the different terminologies, the terminology server providing a graphical user interface that enables graphical navigation of the plurality of terminologies, enables display of a mapping between a first medical term from a first medical terminology to a second medical term from a second medical terminology, and enables coding of pharmacovigilance reports using medical terms of the second terminology based on a description provided using medical terms of the first terminology.

Another system for browsing a pharmacovigilance database with a graphical representation that shows relationships between medical terms in accordance with exemplary embodiments may include means for providing access to a plurality of medical terminologies, and means for mapping medical terms of the plurality of terminologies to a searchable database by using a semantic network to relate the medical terms of the different terminologies. The system may further include means for providing a graphical user interface that enables graphical navigation of the plurality of terminologies, enables display of a mapping between a first medical term from a first medical terminology to a second medical term from a second medical terminology, and enables coding of pharmacovigilance reports using medical terms of the second terminology based on a description provided using medical terms of the first terminology.

These and other features and advantages of the exemplary embodiments will be apparent from the description provided herein.

DETAILED DESCRIPTION OF EXEMPLARY EMBODIMENTS

The description below describes servers, networks, and databases, that may include one or more modules, some of which are explicitly shown in the figures, others that are not. As used herein, the term "module" may be understood to refer to computing software, firmware, hardware, and/or various combinations thereof. It is noted that the modules are exemplary. The modules may be combined, integrated, separated, and/or duplicated to support various applications. Also, a function described herein as being performed at a particular module may be performed at one or more other modules and/or by one or more other devices instead of or in addition to the function performed at the particular module. Further, the modules may be implemented across multiple devices and/or other components local or remote to one another. Additionally, the modules may be moved from one device and added to another device, and/or may be included in multiple devices. It is further noted that the software described herein may be tangibly embodied in one or more physical media, such as, but not limited to, a compact disc (CD), a digital versatile disc (DVD), a floppy disk, a hard drive, read only memory (ROM), random access memory (RAM), as well as other physical media capable of storing software, and/or combinations thereof. Moreover, the figures illustrate various components (e.g., servers, networks, etc.) separately. The functions described as being performed at various components may be performed at other components, and the various components may be combined and/or separated. Other modifications also may be made.

The systems and methods in accordance with exemplary embodiments may be used to meet the challenges of pharmacovigilance. Because of the large amount of pharmacovigilance data, it is difficult to hire enough physicians and pharmacists in pharmacovigilance units of pharmaceutical companies. An increasing number of pharmacovigilance staff are scientists without sufficient medical skills to perform optimal searches in pharmacovigilance databases. Moreover, MedDRA includes a large number of terms and presents high complexity which requires specific training and skills.

The systems and methods in accordance with exemplary embodiments may allow a user to access data in a simple and intuitive way, thereby improving the quality of a search even if queries are performed by pharmacovigilance staff having little skills related to MedDRA and a limited knowledge of medicine. The systems and methods may provide a faster and more exhaustive search of pharmacovigilance databases to allow users to efficiently review and process pharmacovigilance reports without increasing the number of people required to process the data.

The systems and methods in accordance with exemplary embodiments may permit grouping of similar adverse drug reactions for the early detection of medical problems. The systems and methods also may allow for an earlier detection of pharmacovigilance signals, where a signal is a relation between a drug and an adverse effect, this relation being unexpected or insufficiently documented. A better knowledge of adverse drug reactions improves drug safety and thus reduces associated morbi-mortality.

The systems and methods in accordance with exemplary embodiments also may improve searching of different generations of terminologies. For example, controlled terminologies for pharmacovigilance (e.g., WHO-ART and MedDRA) are first generation terminologies. These controlled terminologies, however, are not compatible with the properties of second generation terminologies because the first generation terminologies do not provide any categorical structure and are not compatible with the properties of third generation terminologies because the first generation terminologies do not provide formal definitions. Therefore, users conventionally have been restricted to using high level categories already present in the first generation terminologies without being able to use the categorical structure or formal definitions of the later generation terminologies.

The systems and methods in accordance with exemplary embodiments may offer an improved way to access pharmacovigilance data. The systems and methods may provide a mode of navigation to search for pharmacovigilance data that is more intuitive than conventional systems. In an exemplary embodiment, the systems and methods may improve navigation of pharmacovigilance data by defining WHO-ART and MedDRA terms based on the medical knowledge expressed in SNOMED CT. The improved type of navigation in accordance with exemplary embodiments coupled with searching methods make it possible to find and select relevant pharmacovigilance cases with decreased search times. As will be discussed in further detail below, these functionalities may be based on advanced knowledge representation and inference.

The systems and methods may further provide an implementation of semantic web technologies for browsing pharmacovigilance data. According to World Wide Web Consortium (W3C), "the Semantic Web is the abstract representation of data on the World Wide Web, based on the RDF standards and other standards to be defined. It is being developed by the W3C, in collaboration with a large number of researchers and industrial partners. The Semantic Web brings to the Web the idea of having data defined and linked in a way that it can be used for more effective discovery, automation, integration, and reuse across various applications."

The systems and methods disclosed herein additionally may improve exhaustivity and reliability of search in pharmacovigilance databases to ensure consistent grouping of terms that overcome the limits of conventional terminologies used for coding of adverse drug reactions.

FIG. 1 illustrates a system in accordance with exemplary embodiments. In an exemplary embodiment, the system 100 may permit a user to search for pharmacovigilance reports, to assist the user in coding of terms included in a phamacovigilance report, and to build a customized group of terms. The system 100 in accordance with exemplary embodiments may improve relational knowledge of terms to better group adverse reaction terms related to a common medical condition in order to identify the related pharmacovigilance reports. The system 100 may use knowledge management technologies to allow transferring of relational knowledge from external sources to pharmacovigilance terminologies.

In an exemplary embodiment, the system 100 may provide a terminological resource that links controlled terminologies for pharmacovigilance to a later generation terminology (e.g., third generation terminology). For example, the system 100 may link WHO-ART and MedDRA terms (i.e., first generation terminologies) to synonymous terms in SNOMED CT. It will be appreciated that the system 100 also may be used to link other one or more terminologies to synonymous and/or related terms in other terminologies. For example, the system 100 may benefit from mappings between the controlled terminologies and other terminologies in the metathesaurus of UMLS.

The UMLS is a comprehensive medical knowledge source developed by the National Library of Medicine to enable new information technologies to take advantage of controlled medical vocabularies. The UMLS includes the following major components: the Metathesaurus®, the Semantic Net, and the SPECIALIST Lexicon. The Metathesaurus is a large, multi-purpose, and multi-lingual vocabulary database that contains information about biomedical and health-related concepts, their various names, and the relationships among them. The SPECIALIST Lexicon is a general English lexicon that includes many biomedical terms. Several medical terminologies are mapped one to the other in UMLS. For example several WHO-ART and MedDRA terms are mapped to synonymous SNOMED CT terms.

The system 100 may process WHO-ART and MedDRA terminologies that have controlled terms semantically covering the coding needs of the drug safety domain. The system 100 may overcome the fact that WHO-ART and MedDRA descriptive and diagnostic controlled terms are not sufficiently related, which lowers the precision of statistical analyses and makes it difficult to have a quick overview of a specific medical issue. The system 100 may improve the structures of WHO-ART and MedDRA terminologies to more consistently link the descriptive coding of adverse events with the diagnostic coding of adverse events. The system 100 also may enhance relevant grouping of encoded pharmacovigilance reports, and may be used to build improved terminologies by using a finer terminology having compositional features and controlled terms from drug safety terminologies.

In an exemplary embodiment, the system 100 may include a computer 102 communicatively coupled to a PharmARTS system 104, which is communicatively coupled to a pharmacovigilance database 106. The computer 102 may be a desktop computer, a laptop computer, a workstation, a wireless phone, a wireless device, or other device that may communicate data via a communication network and may display information to a user using a graphical user interface.

Figure 2:
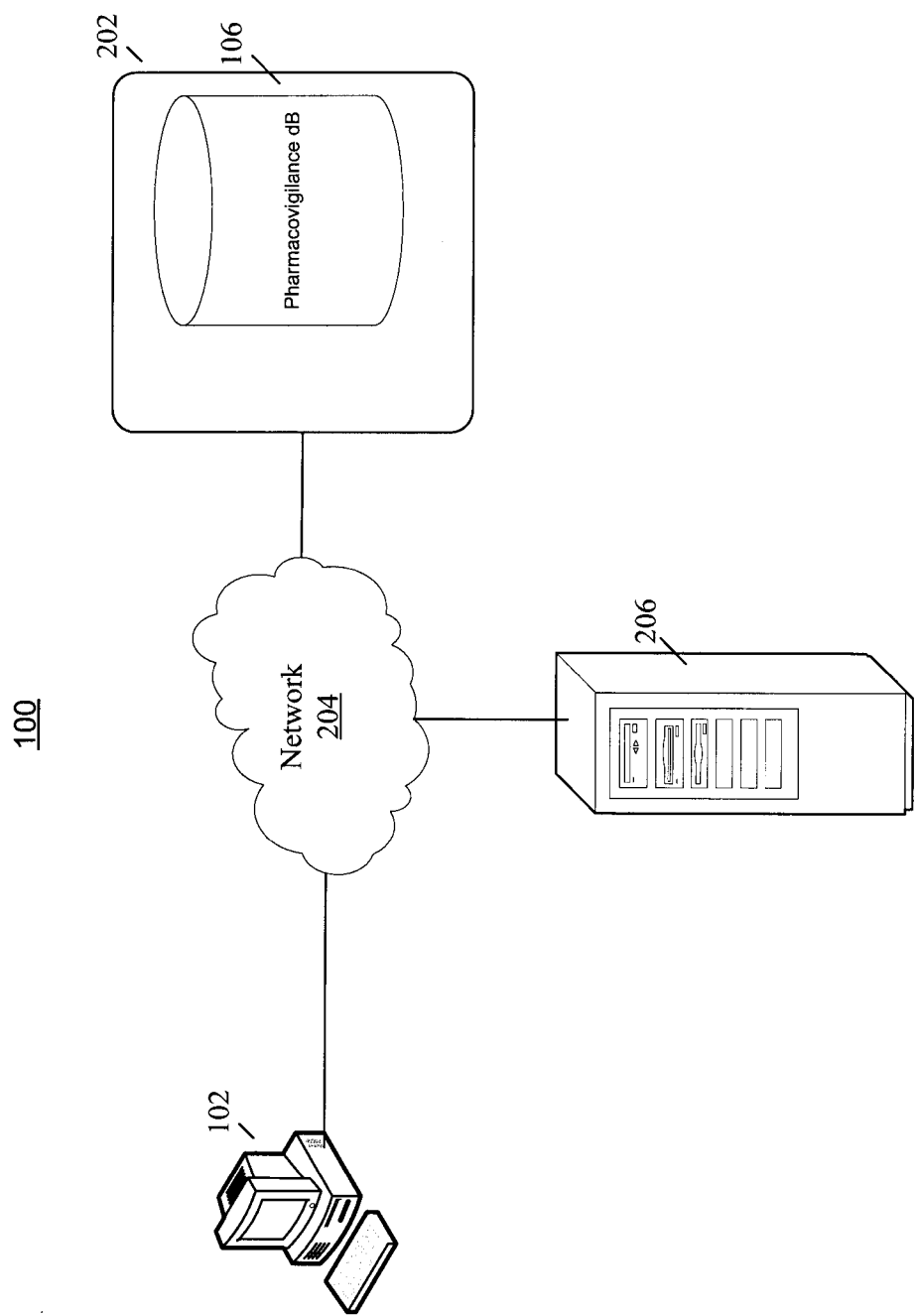
FIG. 2 illustrates an implementation of the system in accordance with exemplary embodiments.

FIG. 2 illustrates an implementation of the system in accordance with exemplary embodiments. In this example, a pharmacovigilance resource server 202 may implement the pharmacovigilance database 106. The pharmacovigilance resource server 202 may be, for example, a relational database management server (RDMS). The pharmacovigilance database 106 may store pharmacovigilance reports. The pharmacovigilance reports may describe adverse drug reactions using controlled terminologies, such as, but not limited to, WHO-ART or MedDRA.

In an exemplary embodiment, the PharmARTS system 104 may be implemented as a PharmARTS terminological server 206 that communicates with the computer 102 via network 204. The PharmARTS terminological server 206 may be a terminology server for coding and providing access to pharmacovigilance data. The network 204 may be wired, wireless, or both, and may use known protocols, such as, but not limited, Internet Protocol (IP) to exchange data between the PharmARTS terminological server 206, the computer 102, and the pharmacovigilance server 202. The PharmARTS terminological server 206 is discussed in further detail below with reference to FIG. 3.

It is noted that system 100 illustrates a simplified view of various components, and that other hardware devices and software not depicted may be included in the system 100. It is also noted that the system 100 illustrates only a single computer 102, a single network 204, a single PharmARTS terminological server 206, and a single pharmacovigilance server 202. It will be appreciated that multiple instances of these devices may be used and/or some or all of these devices may be combined. Moreover, the system 100 also may include other devices not depicted in FIGS. 1-2.

Figure 3:
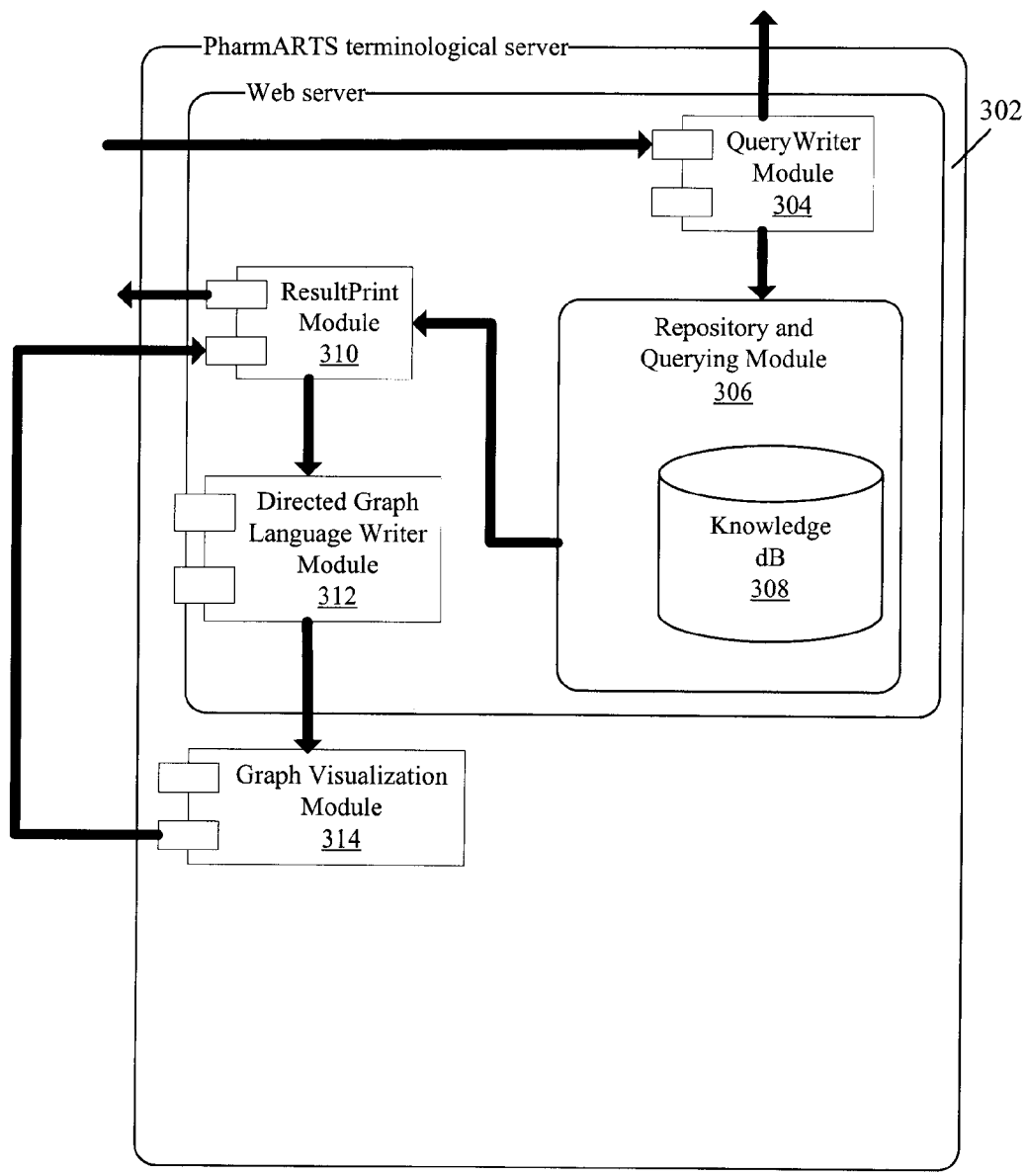
FIG. 3 illustrates various modules of a PharmARTS terminological server in accordance with exemplary embodiments.

FIG. 3 illustrates various modules of the PharmARTS terminological server in accordance with exemplary embodiments. The PharmARTS terminological server 206 may provide services related to the exploitation of the pharmacovigilance server 202. The PharmARTS terminological server 206 may provide graphical navigation of the pharmacovigilance resource server 202 to permit the user of the computer 102 to study a term in its context (e.g., graphical definition and mapping to other terminologies), to contribute to coding of a pharmacovigilance report, and/or to improve access to relevant pharmacovigilance reports. In an exemplary embodiment, the PharmARTS terminological server 206 may be implemented using the Java language (e.g., using Java Server Pages technology on a Tomcat server) based on the Open source Sesame platform. The PharmARTS terminological server 206 also may be implemented using other languages, using other servers, and using other platforms.

The PharmARTS terminological server 206 may allow a user to browse the pharmacovigilance database 106 with graphical representations that show relationships between medical terms used in one or more terminologies. Unlike conventional tools used to access pharmacovigilance data, the PharmARTS terminological server 206 may include formal definitions of terms according to medical criteria and mappings between terminologies. A formal definition is composed of logical assertions describing the relations between medical conditions and associated defining terms. An example of a formal definition is "gastritis has_morphology-inflammation and has_finding_site stomach_structure" where gastritis is a medical condition, has_morphology and has_finding_site are relations, inflammation and stomach_structure are defining terms. Conventional tools do not provide formal definitions of terms and are restricted to text based interfaces where browsing is limited to navigation in the structure of a particular terminology and does not include mappings between different terminologies.

Also unlike conventional tools used to access pharmacovigilance data, the PharmARTS terminological server 206 may store formal definitions in a Repository and Querying facility module. The Repository and Querying facility module may store descriptions of formal definitions in a knowledge database (or other data repository), and may be queried for descriptions of terms from the different controlled terminologies.

Moreover, unlike conventional tools used to access pharmacovigilance data, the PharmARTS terminological server 206 may perform automatic groupings (e.g., using terminological reasoning) of terms based on medical criteria in a dynamic way by restricting or enlarging a query, whereas other tools are constrained by groupings provided by the terminologies.

In an exemplary embodiment, the PharmARTS terminological server 206 may include a web server 302 implementing a Query Writer module 304, a Repository and Querying module 306, a ResultPrint module 310, a Directed Graph Language Writer module 312, and the PharmARTS terminological server 206 also may include a Graph Visualization module 314. It is noted that modules 304-314 are exemplary, and the functions performed by each of the modules 304-314 may be performed by other modules remote or local to the PharmARTS terminological server 206. The modules 304-314 also may be combined and/or their functions may be divided into further submodules. Other modifications also may be made.

The web server 302 may prompt the user for login information when the computer 102 generates a request to access the PharmARTS terminological server 206. The login information may be used to authenticate the user. For example, the login information may be a username, password, code, other information to identify an individual, and/or combinations thereof. Once authenticated, the web server 302 may communicate data via the network 204 to the computer 102 for use in presenting a graphical user interface at the computer 102. The graphical user interface may permit the user to access the resources of the PharmARTS terminological server 206.

The Query Writer module 304 may interact with the user based on information input at a graphical user interface presented to the user at the computer 102. The graphical user interface may be, for example, a web browser that exchanges data with the Query Writer module 304. The user may input a string (i.e., sequence of letters, characters, numerals, or other symbols) or other information that the user desires to be used in a search of pharmacovigilance data. Based on the string received from the computer 102, the Query Writer module 304 may generate and communicate queries to the Repository and Querying module 306. In an exemplary embodiment, the Query Writer module 304 may transform the information received from the computer 102 into a Query Language that may be processed by the Repository and Querying facility. For example, the Query Writer module 304 may generate queries in a query language, such as, but not limited to, the Sesame Resource Description Framework Query Language (SeRQL) and the Resource Description Framework Data Query Language (RDQL). Other query languages also may be used.

The Repository and Querying module 306 may store descriptions of formal definitions in a knowledge database 308 (or other data repository), and may receive queries from the Query Writer module 304 for descriptions of terms from one or more of the controlled terminologies. For example, the Repository and Querying module 306 may be Sesame, which is an open source RDF Schema-based Repository and Querying facility. Other repository and querying facilities also may be used.

The knowledge database 308 may be a searchable database that stores terms of one or more controlled terminologies retrieved from querying the pharmacovigilance database 106. The knowledge database 308 also may store mappings that may identify relationships between the terms of the different terminologies. A graphical depiction of a mapping between terms of different terminologies is provided in FIG. 14, discussed below.

The mapping between the terms of the different terminologies (e.g., between WHO-ART terms and SNOMED-CT terms, between MedDRA terms and SNOMED-CT terms, etc.) may be performed using a semantic network, such as, but not limited to, the Unified Medical Language System (UMLS). The semantic network may include (1) a set of broad subject categories, or Semantic Types, that provide a consistent categorization of all concepts represented in a Metathesaurus, such as, but not limited to, the UMLS Metathesaurus®, and (2) a set of useful and important relationships, or Semantic Relations, that exist between Semantic Types.

For example, PharmARTS terminological server 206 may use the UMLS semantic network to express relations of synonymy between WHO-ART, MedDRA and SNOMED-CT terms. Examples of relations of synonymy may include the WHO-ART term GASTRIC_ULCER, which is synonymous with the MedDRA term Gastric_ulcer and the SNOMED-CT term Unspecified_gastric_ulcer. The United States is particularly interested in mappings between SNOMED-CT and MedDRA terms. For example, the Food and Drug Administration codes every data using SNOMED-CT, but requires coding of pharmacovigilance reports using MedDRA. The mappings between terms of the different terminologies may be used to create a graphical navigation display, which may provide a more intuitive way of reviewing pharmacovigilance data because the definition of the terms of the terminologies (e.g., WHO-ART, MedDRA, etc.) may be based on the medical knowledge expressed in a different terminology (e.g., SNOMED CT).

Figure 18:
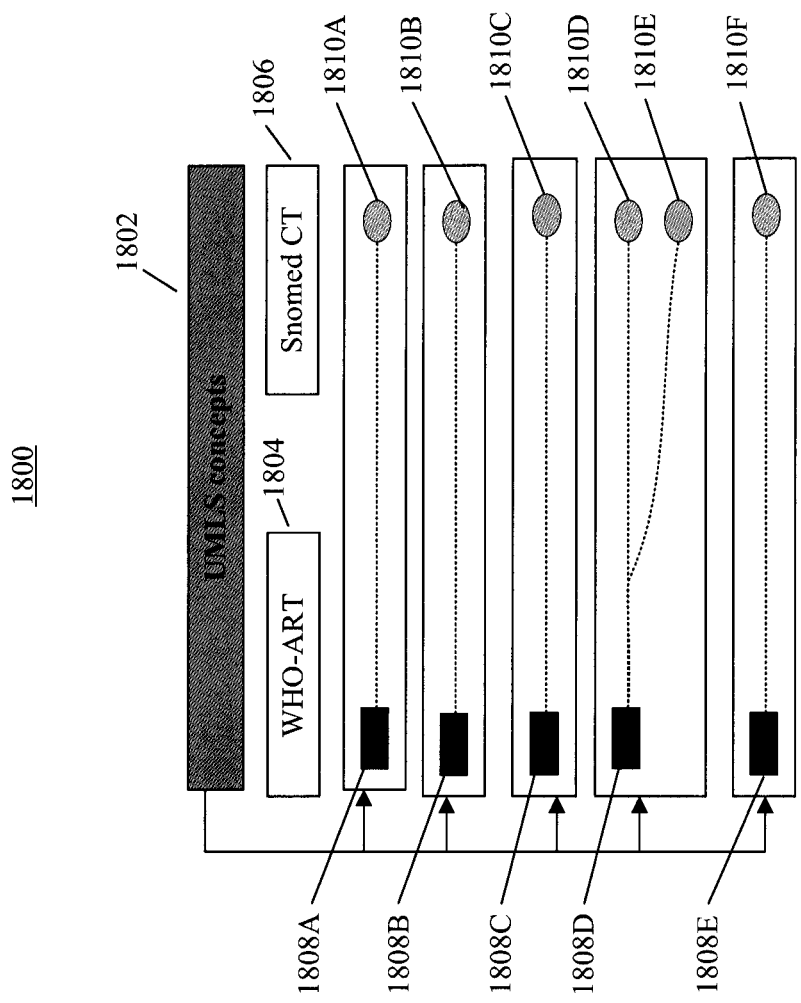
FIG. 18 illustrates a semantic network expressing relations of synonymy between terms of different terminologies in accordance with exemplary embodiments.

FIG. 18 illustrates a semantic network expressing relations of synonymy 1800 between the terms of the different terminologies in accordance with exemplary embodiments. In this example, the PharmARTS terminological server 206 may use concepts of an UMLS semantic network 1802 to express relations of synonymy between WHO-ART preferred terms 1808A-E of the WHO-ART terminology 1804 and SNOMED CT terms 1810A-E of the SNOMED CT terminology 1806. The concepts of the UMLS semantic network 1802 may group synonymous terms from different terminologies. For example, the UMLS semantic network 1802 may extract a mapping list between WHO-ART preferred terms 1808A-E and their synonym SNOMED-CT terms 1810A-F. As depicted, each WHO-ART preferred term 1808 may relate to at least one synonymous SNOMED-CT term 1810. In this example, the WHO-ART preferred term 1808A is synonymous with SNOMED-CT term 1810A, the WHO-ART preferred term 1808B is synonymous with SNOMED-CT term 1810B, the WHO-ART preferred term 1808C is synonymous with SNOMED-CT term 1810C, the WHO-ART preferred term 1808D is synonymous with both SNOMED-CT terms 1810D and 1810E, and the WHO-ART preferred term 1808E is synonymous with SNOMED-CT term 1810F. It is noted that FIG. 18 illustrates an example of applying a semantic network to identify synonyms between WHO-ART and SNOMED-CT terms. The semantic network also may be used to identify synonyms between other terminologies. Moreover, the semantic network also may be used to identify relationships based on morphology, topography, function, etiological, or other relationships between medical terms used in different medical terminologies. After the relationships (i.e., synonyms) have been identified, the PharmARTS terminological server 206 may create a hierarchy for the related terms.

Figure 19:
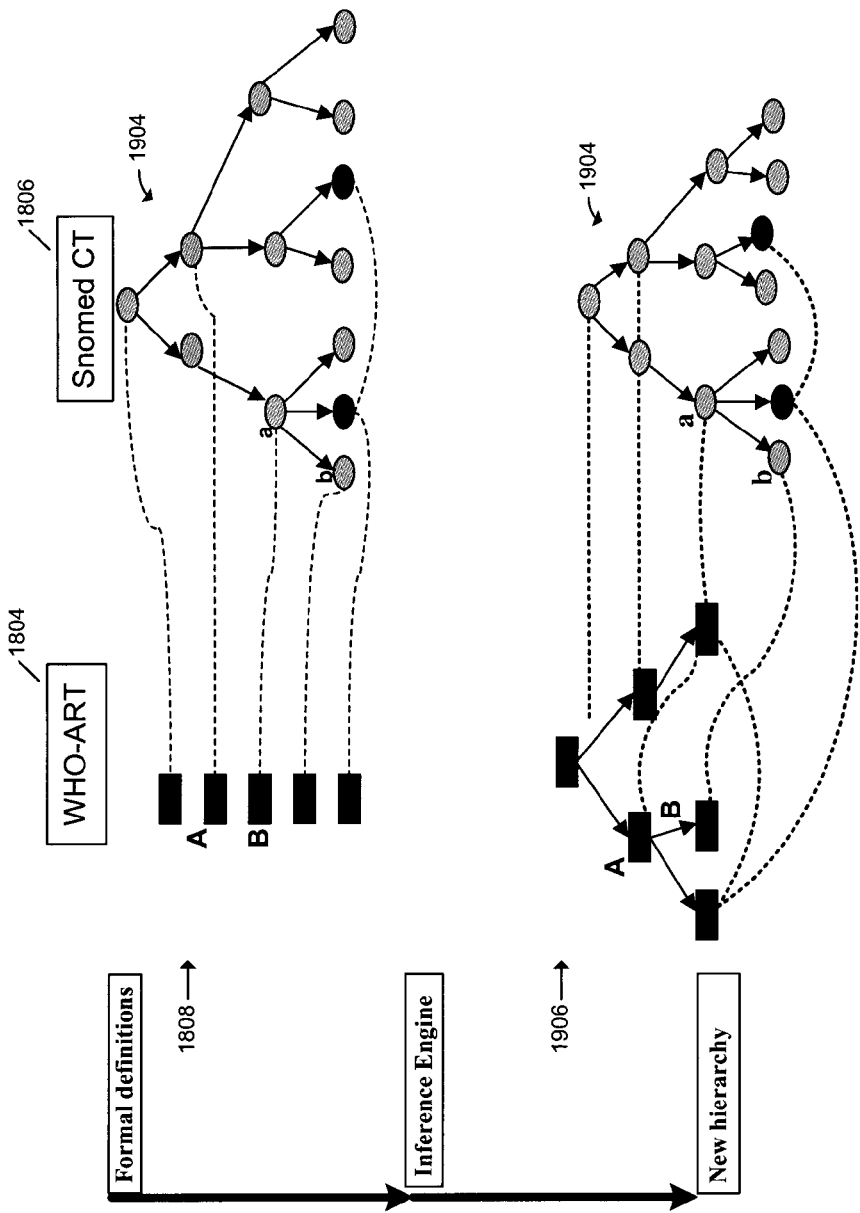
FIG. 19 illustrates creating a hierarchy for a terminology in accordance with exemplary embodiments.

FIG. 19 illustrates creating a hierarchy for a terminology in accordance with exemplary embodiments. In an exemplary embodiment, the PharmARTS terminological server 206 may create formal definitions for the terms of the terminology, may apply an inference engine to classify the formal definitions, and may create a hierarchy based on the classification engine. The relations between the terms of the different terminologies may be expressed by means of the Web Ontology Language (OWL) formalism for knowledge representation. Other formalisms also may be used. The OWL formalism may be used to create a hierarchy for a terminology based on a different terminology. For example, PharmARTS terminological server 206 may use the mapping relations between the terms of the different terminologies to structure the WHO-ART terms 1808 to create a WHO-ART hierarchy 1906 for the WHO-ART terminology 1804 based on a SNOMED-CT hierarchy 1904. As depicted, FIG. 19 includes a dotted line between the WHO-ART terms 1808 and the one or more synonymous SNOMED-CT terms 1810 included in the SNOMED-CT hierarchy 1904.

An inference engine may then classify the WHO-ART terms 1808 to a particular level within the SNOMED-CT hierarchy 1904. The inference engine may be, for example, the Racer Pro inference engine. Other inference engines also may be used.

After the classification phase, the PharmARTS terminological server 206 may rewrite the relations expressed in OWL in the Resource Description Framework (RDF) formalism for knowledge representation. For example, the RDF formalism may express a terminology as a network with labeled arcs. Generally, any formalism other than RDF that is able to deal with structures composed of three elements also may be used. These three elements may be 1) a term from a controlled terminology (e.g., WHO-ART or MedDRA); 2) a relation (e.g., "has_finding_site" or "has_morphology"), and 3) a value of fact. For example, the triple composed of the following elements 1) Gastric_ulcer; 2) has_finding_site; 3) Stomach_structure can be described according to several knowledge based formalisms that may be used in the PharmARTS system. The mapping also may be performed manually or using natural language processing.

The PharmARTS terminological server 206 may then create the hierarchy 1906 for the terminology based on the mapping. For example, the PharmARTS terminological server 206 may create and store a WHO-ART hierarchy 1906 based on the SNOMED CT hierarchy 1904 in the knowledge database 308. After the mappings between the terms of the different terminologies have been created and stored in the knowledge database 308, the Query Writer module 304 of the PharmARTS terminological server 206 may receive search requests from the computer 102 requesting to search the knowledge database 308. As discussed above, the Query Writer module 304 may generate a query based on the search request and may communicate the query to the Repository and Querying module 306.

In response to the query from the Query Writer module 304, the Repository and Querying module 306 may search the knowledge database 308 and may generate query results. The query results may be some or all of the terms in one or more of the terminologies in the knowledge database 308 identified as matching the string received from the user, as well as mappings to any other terms related to the terms matching the string in a same or different terminology. The Repository and Querying module 306 may communicate the query results to the ResultPrint Module 310.

The ResultPrint module 310 may process the query results returned by the Repository and Querying module 306 for on-screen display at the computer 102. In an exemplary embodiment, the ResultPrint module 310 may format the query results in graphical user interface data for display at a graphical user interface at the computer 102, and may communicate the graphical user interface data to the computer 102. When the user of the computer 102 requests to graphically view the relationships between the terms, the ResultPrint module 310 may communicate the query results to a Directed Graph Language Writer module 312.

The Directed Graph Language Writer module 312 may translate the query results into a graphical representation using a graph description language, such as, but not limited to, the DOT language. Generally, any graph description language that is able to describe a graph and optionally format arcs color and nodes shapes may be used. The graphical representation may be used to display a graphical navigation display at the computer 102. Once the graphical representation is fully described in the graph description language, the Directed Graph Language Writer module 312 may communicate the graphical representation to a Graph Visualization module 314.

The Graph Visualization module 314 may use a graph language, such as, but not limited to, GraphViz, to generate an image file, such as, but not limited to, a Joint Photographic Experts Group (JPEG) file. Generally, any graph language that is able to describe a graph and optionally format arcs color and nodes shapes may be used. The Graph Visualization module 314 may then communicate the image file to the ResultPrint module 310.

The ResultPrint module 310 may then integrate the image file into a graphical navigation display included in a graphical user interface presented to the user. For example, ResultPrint module 310 may integrate the image file into a webpage that is communicated to the computer 102 for display to the user. In an exemplary embodiment, the webpage may be an abstract representation of data on the World Wide Web, based on the RDF standards and/or on other standards. The webpage may be used to examine data defined and linked in a way that it can be used for more effective discovery, automation, integration, and reuse across various applications.

After the user identifies a term or group/cluster of terms included in the graphical navigation display, the user may instruct the computer 102 to communicate a pharmacovigilance report request to the Query Writer module 304 based on the identified term or group/cluster of terms to request one or more pharmacovigilance reports, as will be described in further detail below.

Figure 4:
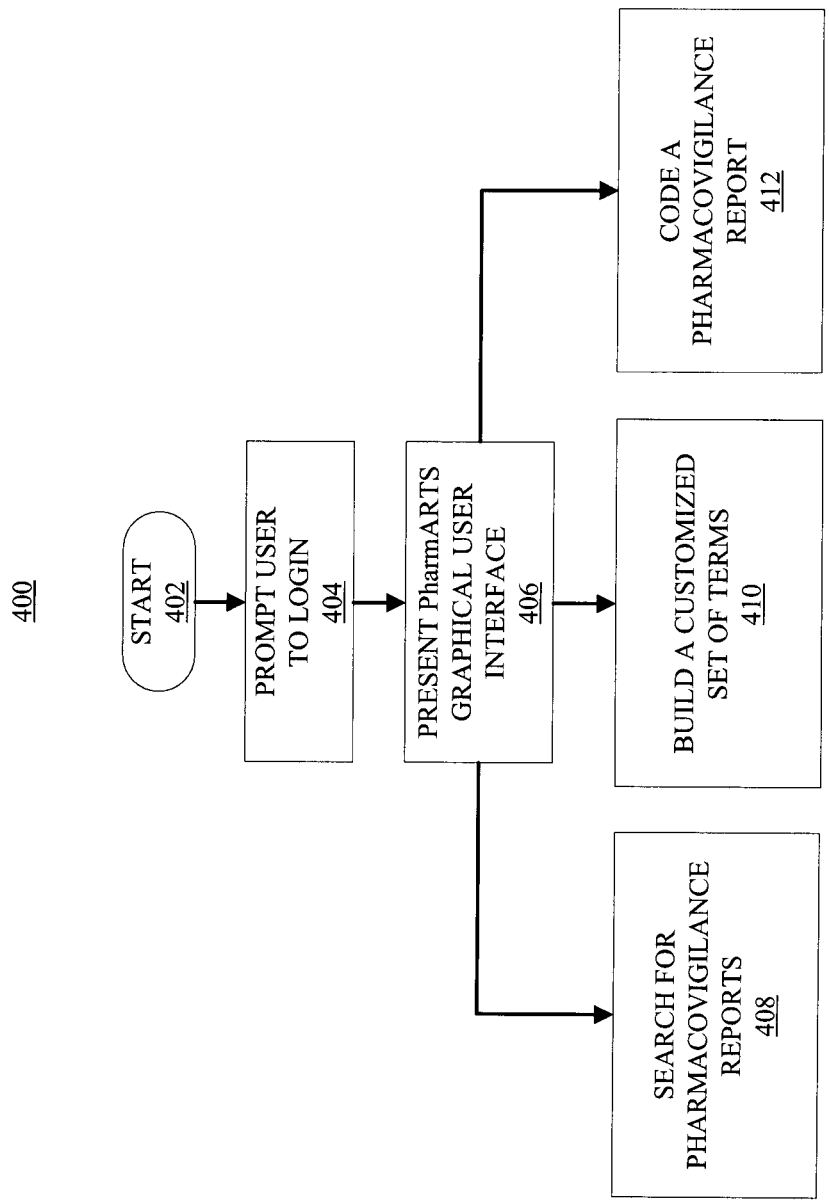
FIG. 4 illustrates a method for logging in a user to a PharmARTS system in accordance with exemplary embodiments.

FIG. 4 illustrates a method for logging in a user to the PharmARTS system in accordance with exemplary embodiments. This exemplary method is provided by way of example, as there are a variety of ways to carry out methods disclosed herein. The method 400 shown in FIG. 4 can be executed or otherwise performed by one or a combination of various systems. The method 400 is described below as carried out by the system 100 shown in FIGS. 1-3 by way of example, and various elements of the system 100 are referenced in explaining the example method of FIG. 4. Each block shown in FIG. 4 represents one or more processes, methods, or subroutines carried in the exemplary method 400.

Referring to FIG. 4, the exemplary method 400 may begin at block 402 and may continue to block 404.

In block 404, the method 400 may include prompting a user to login to the PharmARTS system 104. In an exemplary embodiment, the web server 302 may communicate data to the computer 102 via the network 204 to present a graphical user interface prompting the user to login to the PharmARTS system 104. For example, the graphical user interface may be a web browser. The user may submit authentication information to authenticate the user to the PharmARTS system 104. The PharmARTS system 104 may permit several users to connect simultaneously to use the PharmARTS services. Once the one or more users are authenticated, the method 400 may continue to block 406.

In block 406, the method may include communicating data useable for presenting a PharmARTS graphical user interface at the computer. In an exemplary embodiment, the web server 302 may communicate graphical user interface data to the computer 102 via the network 204. The computer 102 may receive the graphical user interface data and may present a PharmARTS graphical user interface to the user. The PharmARTS graphical user interface may prompt the user to select at least one of searching for pharmacovigilance data, building a custom set of terms, and/or coding a pharmacovigilance report. The method 400 may continue to block 408 if the user selects to search for pharmacovigilance data, may continue to block 410 if the user selects to build a custom set of terms, and may continue to block 412 if the user selects to code a pharmacovigilance report. A further discussion of a user selecting to search for pharmacovigilance data, building a custom set of terms, and coding a pharmacovigilance report is discussed below with relation to FIG. 5.

Figure 5:
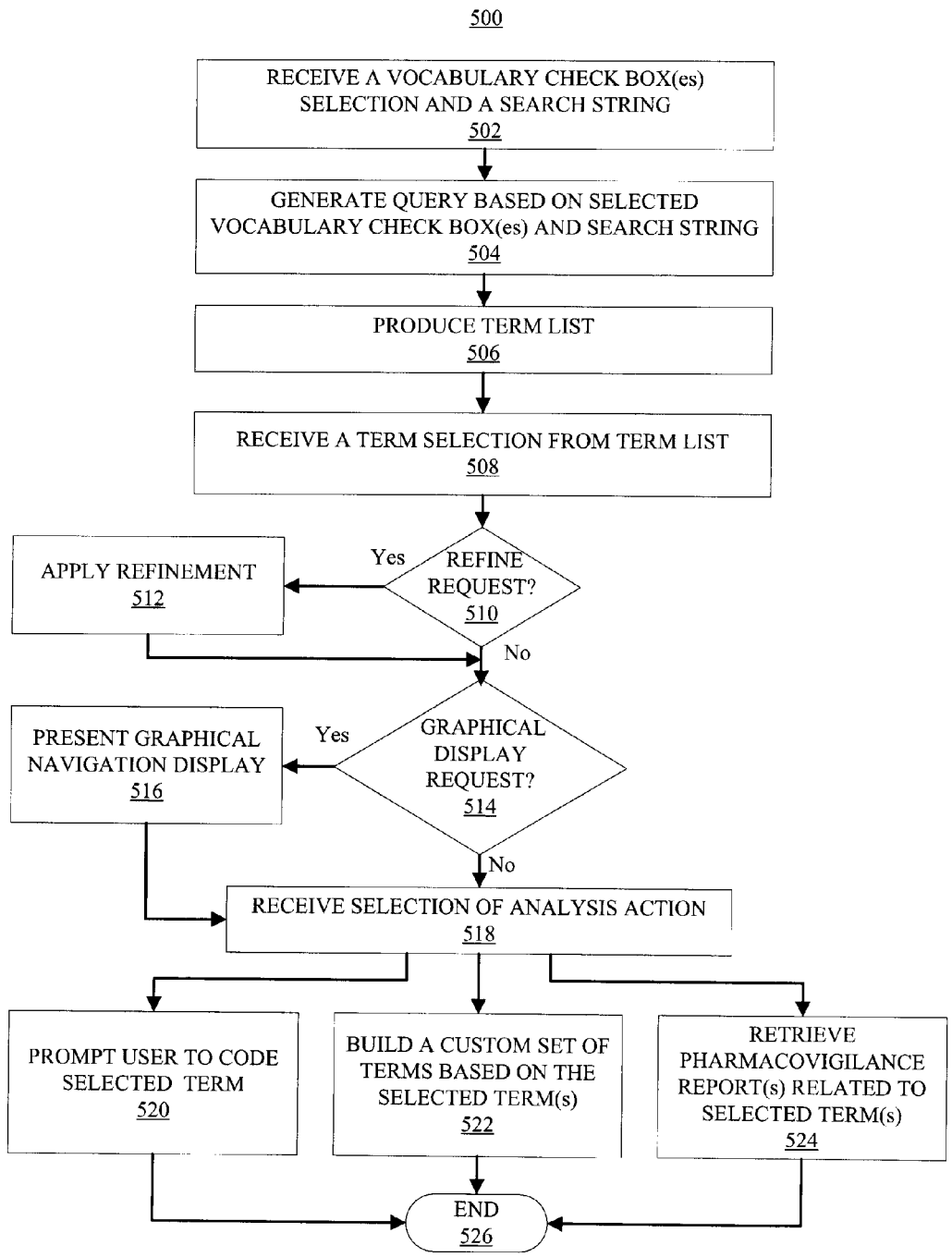
FIG. 5 illustrates a method for interacting with a PharmARTS terminological server via a PharmARTS graphical user interface in accordance with exemplary embodiments.

FIG. 5 illustrates a method for interacting with the PharmARTS terminological server via the PharmARTS graphical user interface in accordance with exemplary embodiments. This exemplary method is provided by way of example, as there are a variety of ways to carry out methods disclosed herein. The method 500 shown in FIG. 5 can be executed or otherwise performed by one or a combination of various systems. The method 500 is described below as carried out by the system 100 shown in FIGS. 1-3 by way of example, and various elements of the system 100 are referenced in explaining the example method of FIG. 5. Each block shown in FIG. 5 represents one or more processes, methods or subroutines carried in the exemplary method 500. Referring to FIG. 5, the exemplary method 500 may begin at block 502.

In block 502, the method may include receiving a vocabulary check box selection and a search string from information input by a user in a PharmARTS graphical user interface. In an exemplary embodiment, the web server 302 may create graphical user interface data instructing the computer 102 to present a PharmARTS graphical user interface to the user. The PharmARTS graphical user interface may prompt the user to select one or more vocabulary check boxes and to enter a search string.

Figure 6:
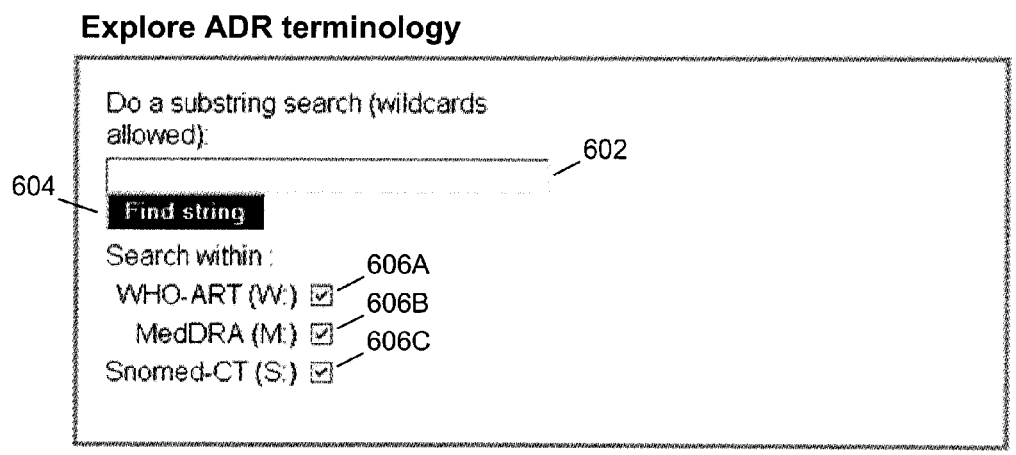
FIG. 6 illustrates a PharmARTS graphical user interface in accordance with exemplary embodiments.

FIG. 6 illustrates a PharmARTS graphical user interface in accordance with exemplary embodiments. In an exemplary embodiment, the PharmARTS graphical user interface 600 may include a search field 602, a find string field 604, and one or more vocabulary check box fields 606A-C. It is noted that the term field may be used to represent a button, an icon, or other displayable item that the user may select in a graphical user interface. The user may type a desired search string into the search field 602. In this example, the PharmARTS graphical user interface includes three vocabulary check box fields 606A-C, with vocabulary check box field 606A being associated with the terms included in the WHO-ART terminology, with vocabulary check box field 606B being associated with the terms included in the MedDRA terminology, and with vocabulary check box field 606C being associated with the terms included in the SNOMED CT terminology. It is noted that the vocabulary check box fields 606A-C, and other terminology that include a controlled vocabulary of terms, and/or more or fewer vocabulary check box fields 606A-C may be included in the PharmARTS graphical user interface 600. Referring again to FIG. 5, after the user has selected one or more vocabulary check boxes and input a search string, the method 500 may continue to block 504.

In block 504, the method may include generating a query based on the selected vocabulary check box(es) and the search string. In an exemplary embodiment, the Query Writer module 304 of the PharmARTS system 104 may generate a query based on the selected one or more vocabulary check boxes and the entered search string. The Query Writer module 304 may communicate the query to the Repository and Querying Module 306 to search the knowledge database (dB) 308. The pharmacovigilance resource server 202 may search the pharmacovigilance database 106 based on the query, and may respond to the query with query results.

Figure 20:
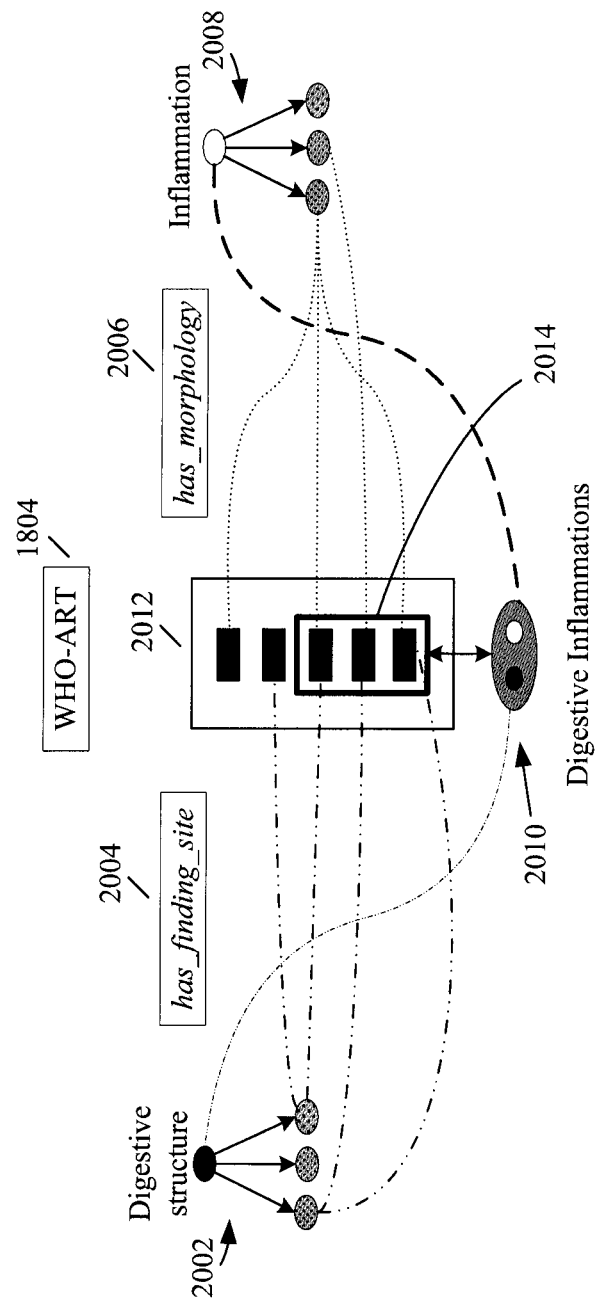
FIG. 20 illustrates performing a restriction query in accordance with exemplary embodiments.

FIG. 20 illustrates a process of creating a query in accordance with exemplary embodiments. In this example, the candidate terms 2012 are WHO-ART terms 1804 that are related by a has_morphology relationship 2006 to defining nodes 2008 for concepts that are equivalent or more specific than Inflammation and that are related by a has_finding_site relationship 2004 to defining concepts 2002 that are equivalent or more specific than "digestive structure." A "digestive inflammation" query 2010 for all inflammation localized in digestive structure will bring up the candidate terms 2014 that are both related to inflammation and digestive structure. Referring again to FIG. 5, the method 500 may then continue to block 506.

In block 506, the method may include producing a term list based on the query results. In an exemplary embodiment, the ResultPrint module 310 may receive the query results from the pharmacovigilance server 202. The query results may include a term list of candidate terms and defining terms. The ResultPrint module 310 may generate a term list based on the query results and may communicate the term list to the computer 102 via the network 204. The computer 102 may cause display of the term list to the user in the PharmARTS graphical user interface in a term list display.

Figure 7:
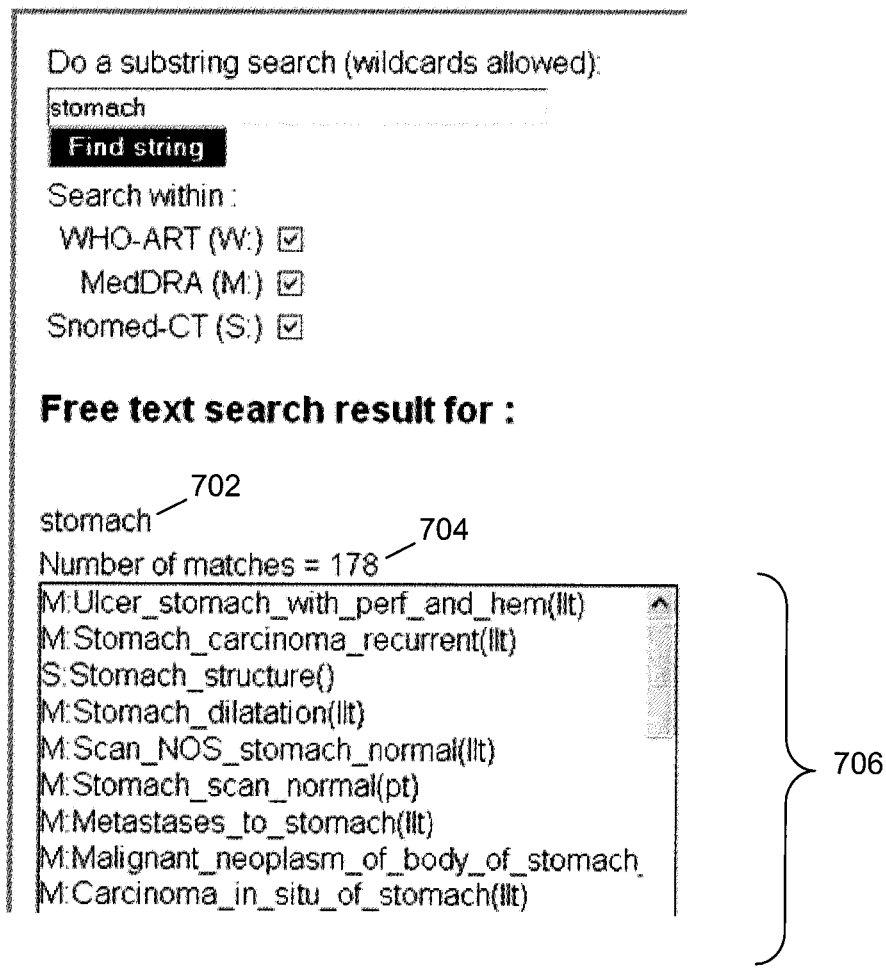
FIG. 7 illustrates a term list display of a PharmARTS graphical user interface in accordance with exemplary embodiments.

FIG. 7 illustrates a term list display of the PharmARTS graphical user interface 600 in accordance with exemplary embodiments. The term list display may display a list of candidate terms and defining terms retrieved from the query. The term list display of the PharmARTS graphical user interface 600 displays the search string included in the query in a search string field 702, a number of matches identified in the search results for the search string in a number of matches field 704, and a term list for the matching terms in the search results for the search string in the defining term list field 706.

In the example depicted in FIG. 7, the user requested a search based on the search string "stomach." The search string field 702 displays the search string 702, and the number of matches field 704 identifies that there are one hundred and seventy eight matches for the search string. The PharmARTS terminological server 206 may identify a match with a medical term included in one or more of the medical terminologies if the search string is included in the medical term. In an exemplary embodiment, the defining term list field 706 may display some or all of the WHO-ART, MedDRA and/or SNOMED CT terms that contain the search string. For example, the search string "stomach" is contained within the SNOMED CT term "stomach_structure." In the defining term list field 706, the M: prefix stands for MedDRA, the S: prefix stands for SNOMED-CT and the W: prefix stands for WHO-ART. The terms in the defining term list field 706 are "defining terms" that are related to the definitions of pharmacovigilance report coding terms. The method 500 may continue to block 508.

In block 508, the method may include receiving a user selection of a defining term from the term list and causing display of candidate terms associated with the selected defining term. In an exemplary embodiment, the user may select a defining term from the defining terms displayed in the defining term list field 706 in the PharmARTS graphical user interface 600. In response to the selection, the PharmARTS system 104 may update the PharmARTS graphical user interface 600 to cause display of candidate terms associated with the selected defining term in a candidate term list field including one or more candidate terms. For example, the user may click on a defining term from the defining term list field 706 and the PharmARTS graphical user interface 600 may display the candidate term list field including one or more candidate terms. The candidate terms may belong to a standard terminology used in coding pharmacovigilance reports.

FIG. 8 illustrates a PharmARTS graphical user interface after the user has selected a defining term in accordance with exemplary embodiments. The PharmARTS graphical user interface 600 may include a candidate term list field 804. In this example, the defining terms displayed in the defining term list field 706 are SNOMED CT terms and the candidate terms displayed in the candidate term list field 804 are WHO-ART terms. The candidate terms displayed in the candidate term list field 804 may be based on the mappings included in the knowledge database 308. The candidate terms may be synonyms of the defining terms, may be morphologically described by the defining terms, may be topographically described by the defining terms, may be functionally described by the defining terms, may be etiologically described by the defining terms, may be described by other relationships with the defining terms, and/or combinations thereof. The method 500 may then continue to block 510.

In block 510, the method may include determining whether a refinement request has been received to refine the candidate terms. In an exemplary embodiment, the PharmARTS system 104 may permit the user to refine the candidate terms included in the candidate term list field 804 by creating logical relations between the defining terms. For example, the user may use Boolean operators, such as, but not limited to, the Boolean AND operator and the Boolean OR operator, to create logical relations between the defining terms (e.g., stomach AND hemorrhage). If the PharmARTS system 104 receives a refinement request, the method 500 may continue to block 512. If the PharmARTS system 104 does not receive a refinement request, the method may continue to block 514.

In block 512, the method may include applying the requested refinement to the query. In an exemplary embodiment, the PharmARTS graphical user interface 600 may permit the user to restrict the query, to enlarge the query, to clear a previous restriction, to clear the query, and/or combinations thereof. The refinements may be used, for example, when the list of "candidate terms" is too large and/or when the user has identified in the pharmacovigilance report verbatim other features that could be used as defining terms.

If the refinement request is to clear a restriction, the PharmARTS system 104 may clear a restriction on the query results. Referring again to FIG. 8, in an exemplary embodiment, the user may select the clear restriction field 816. Selecting the clear restriction field 816 may instruct the PharmARTS system 104 to clear a restriction on the query results. For example, the clear restriction field 816 may be used to eliminate a logical relationship (e.g., AND operator) with the last defining term (or other selected defining term). The clear restriction field 816 may modify a restriction on a query from being stomach AND hemorrhage to create a new query based on stomach.

If the refinement request is to clear a query, the PharmARTS system 104 may clear a query. Referring again to FIG. 8, in an exemplary embodiment, the user may select the clear query field 810 in the PharmARTS graphical user interface 600. Selecting the clear query field 810 may instruct the PharmARTS system 104 to delete all of the defining terms in the defining term list field 706.

If the refinement request is to restrict a query, the PharmARTS system 104 may create a restriction on a query. Referring again to FIG. 8, in an exemplary embodiment, the user may select the restriction field 812 in the PharmARTS graphical user interface 600. Selecting the restriction field 812 may instruct the PharmARTS system 104 to generate a list of candidate terms defined simultaneously by two or more defining terms. For example, the PharmARTS system 104 may restrict the query results to the candidate terms being related to both a first defining term and a second defining term (e.g., stomach_structure AND hemorrhage). An example of restricting a query is provided in the query field 806 where the query is based on stomach_structure AND hemorrhage.

Figure 9:
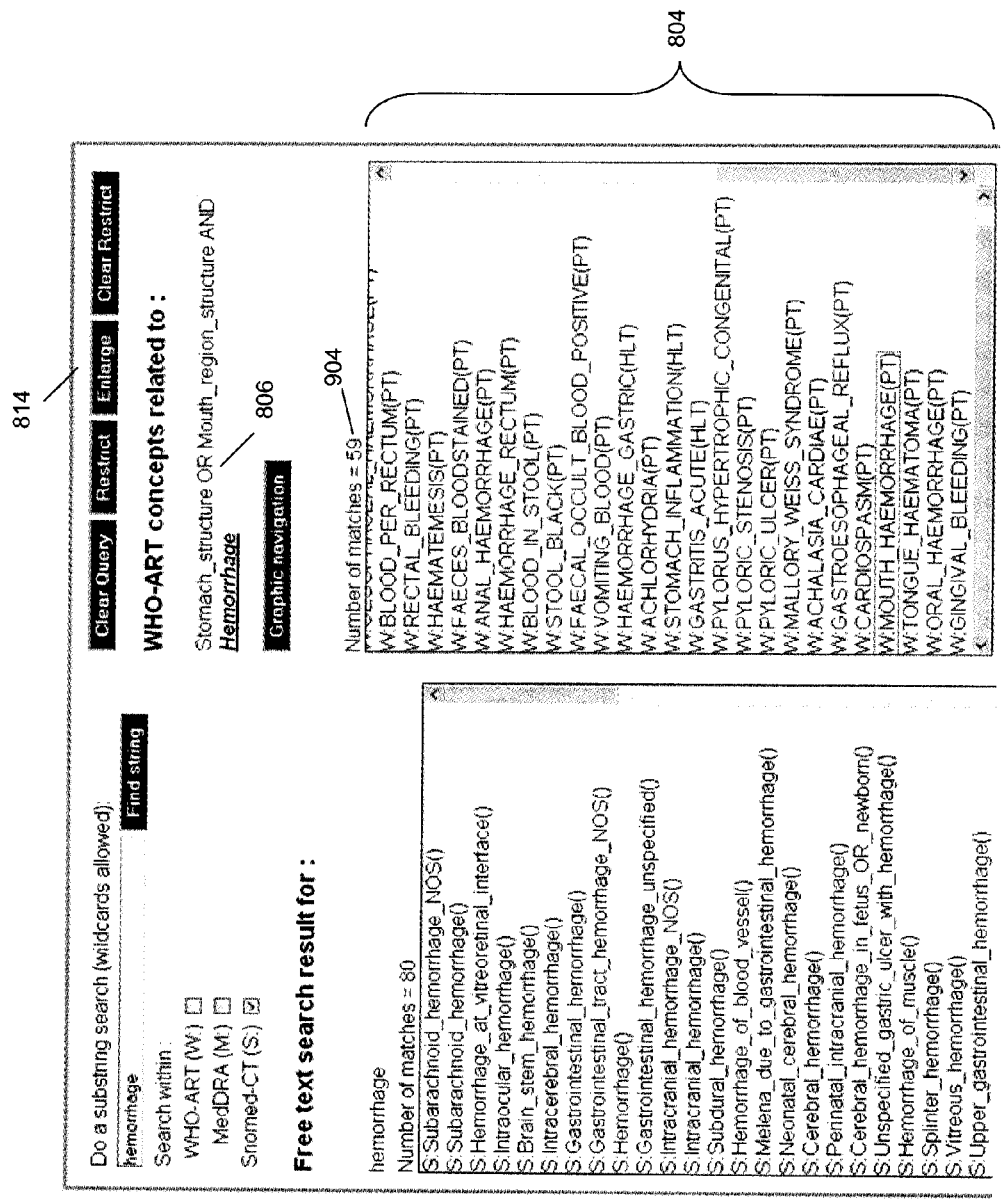
FIG. 9 illustrates enlarging a query in accordance with exemplary embodiments.

If the refinement request is to enlarge a query, the PharmARTS system 104 may enlarge the query. FIG. 9 illustrates enlarging a query in accordance with exemplary embodiments. In an exemplary embodiment, the user may select the enlarge query field 814 in the PharmARTS graphical user interface 600. Selecting the enlarge query field 814 may instruct the PharmARTS system 104 to enlarge the query results to the candidate terms being related to at least one of a list of selected defining terms (e.g., stomach_structure OR hemorrhage). An example of restricting a query is provided in the query field 806 where the query is based on stomach_structure OR mouth_region_structure AND hemorrhage. In this example, the query may then return fifty nine matches in the number of matches field 904 and may update the candidate list in the candidate term list field 804. The method 500 may then continue to block 514.

In block 514, the method may include determining whether the user has selected a graphical navigation display request field. In an exemplary embodiment, the PharmARTS graphical user interface 600 may include a graphical navigation display request field 808. Selecting the graphical navigation display request field 808 may instruct the PharmARTS system 104 to display a graphical navigation display. The graphical navigation display may graphically depict a relationship between the defining terms and the candidate terms. The graphical navigation display may be used to refine a term list that includes defining terms and one or more candidate terms by graphically navigating in the graphical navigation display. The graphical navigation display will be discussed in further detail below with reference to FIGS. 11-18. If the graphical navigation display request field 808 is not selected, the method 500 may continue to block 518. If the graphical navigation display request field 808 is selected, the method 500 may continue to block 516.

In block 516, the method may include causing display of the graphical navigation display. In an exemplary embodiment, the PharmARTS system 104 may update the PharmARTS graphical user interface 600 to cause display of the graphical navigation display at the computer 102. The method 500 may continue to block 518.

In block 518, the method 500 may include receiving a selection of an analysis action. In an exemplary embodiment, the user may select an analysis field in the PharmARTS graphical user interface 600. Referring again to FIG. 8, the PharmARTS graphical user interface 600 may include three analysis fields: a "Go to detailed pharmacovigilance cases" field 820, a "pharmacovigilance report searching" field 822, and a "build customized set of terms" field 824. If the user selects the "Go to detailed pharmacovigilance cases" field 820, the method 500 may continue to block 520. If the user selects "build customized set of terms" field 824, the method 500 may continue to block 522. If the user selects the "pharmacovigilance report searching" field 822, the method 500 may continue to block 524.

In block 520, the method may include prompting the user to code the selected term in a pharmacovigilance report. In an exemplary embodiment, once the user has created a relevant list of candidate terms, the user may choose the one or more most relevant terms and completes his report.

Figure 10:
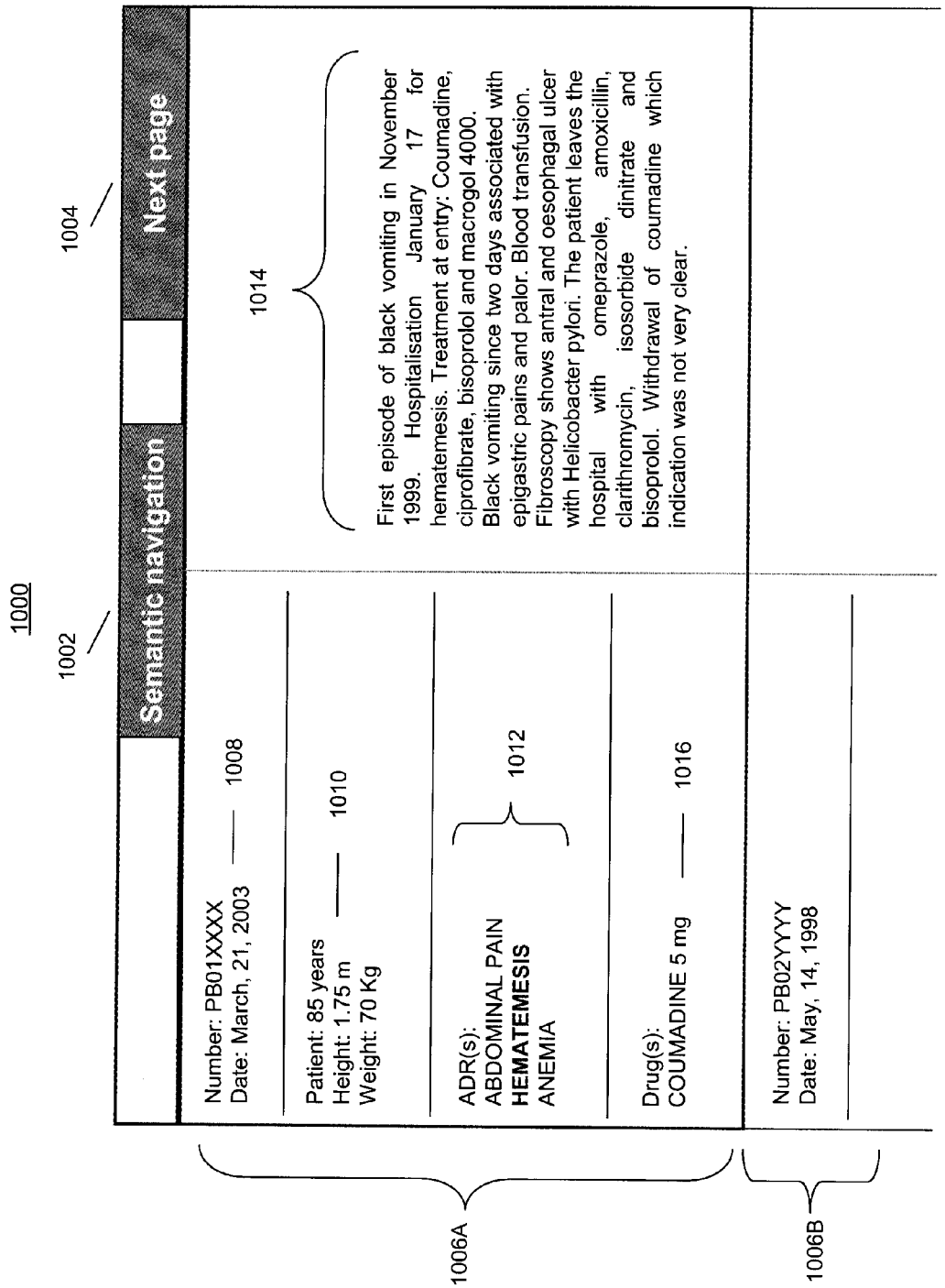
FIG. 10 illustrates a pharmacovigilance report in accordance with exemplary embodiments.

FIG. 10 illustrates a pharmacovigilance report in accordance with exemplary embodiments. The pharmacovigilance reports 1000 may be displayed when the user selects the list of candidate terms by selecting the "Go to detailed pharmacovigilance cases" field 820. The pharmacovigilance cases that contain one or more terms from the list of candidate terms are displayed. The pharmacovigilance report 1000 may include a next page/previous field 1004 to permit the user to navigate through the pharmacovigilance report 1000.

In an exemplary embodiment, the pharmacovigilance report 1000 is an example of browsing a pharmacovigilance report related to a set of terms. This figure depicts two pharmacovigilance cases 1006A-B. The user may select the semantic navigator button 1002 that sends the user back to the PharmARTS graphical user interface 600 presented in FIG. 8. Each pharmacovigilance case 1006 may include of a report number and date 1008, a patient age, height, and weight field 1010, a list of adverse drug reactions coded using a controlled terminology field 1012, a narrative field 1014, and a list of drugs field 1016. The narrative 1004 may contain a full text description of the patient history and the adverse drug reactions. Referring again to FIG. 5, this branch of the method 500 may continue to block 526 and end.

In block 522, the method may include prompting the user to build a custom set of terms. In an exemplary embodiment, the user may select the Build Customized Set of Terms field 824 in the PharmARTS graphical user interface 600 once the user has identified a relevant list of candidate terms. Selecting the Build Customized Set of Terms field 824 may save this list of candidate terms and may perform queries on the pharmacovigilance database 106 using this list. This branch of the method 500 may continue to block 526 and end.

In block 524, the method may include prompting the user to retrieve one or more pharmacovigilance reports. In an exemplary embodiment, the PharmARTS system 104 may request from the pharmacovigilance database 106 one or more pharmacovigilance reports coded with at least one of the terms from the candidate list. Referring again to FIG. 8, in an exemplary embodiment, the user may select the "Go to detailed pharmacovigilance cases" field 820 in the PharmARTS graphical user interface 600. The PharmARTS system 104 may retrieve one or more pharmacovigilance reports coded with at least one of the terms from the selected list of candidate terms and may communicate the one or more pharmacovigilance reports to the computer 102. An example of a phamacovigilance report is depicted in FIG. 10. The computer 102 may receive the pharmacovigilance report and the user may navigate through the pharmacovigilance report. This branch of the method 500 may continue to block 526 and end.

To assist the user in at least one of searching for pharmacovigilance data, building a custom set of terms, and/or coding a pharmacovigilance report, the PharmARTS system 104 may graphically present relationships between the candidate terms and/or the defining terms in a graphical navigation display.

Figure 11:
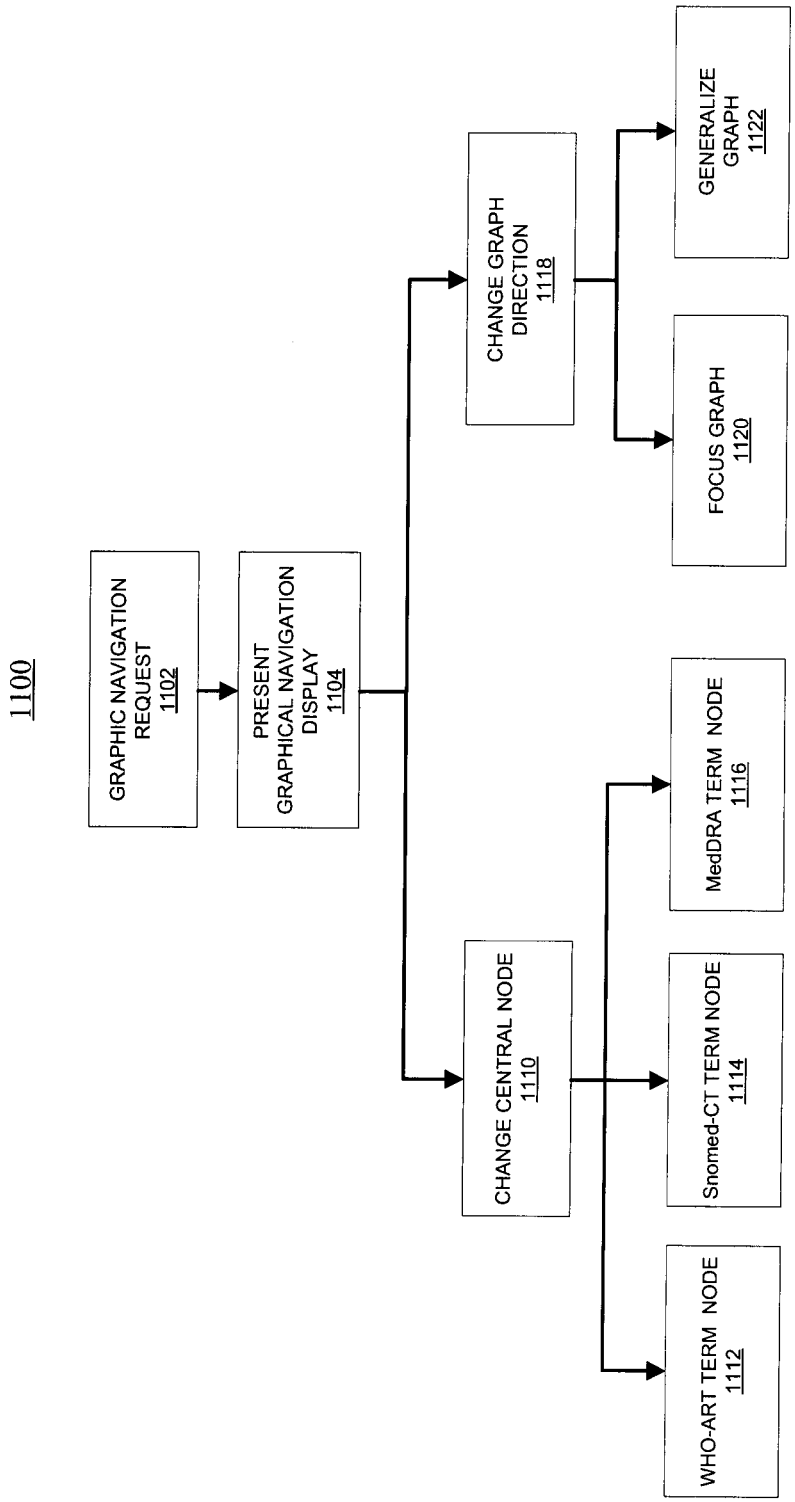
FIG. 11 illustrates a method of providing a graphical navigation display in accordance with exemplary embodiments.

FIG. 11 illustrates a method of providing a graphical navigation display in accordance with exemplary embodiments. This exemplary method is provided by way of example, as there are a variety of ways to carry out methods disclosed herein. The method 1100 shown in FIG. 11 can be executed or otherwise performed by one or a combination of various systems. The method 1100 is described below as carried out by the system 100 shown in FIGS. 1-3 by way of example, and various elements of the system 100 are referenced in explaining the example method of FIG. 11. Each block shown in FIG. 11 represents one or more processes, methods, or subroutines carried in the exemplary method 1100. Referring to FIG. 11, the exemplary method 1100 may begin at block 1102.

In block 1102, the method may include receiving a graphic navigation request. Referring again to FIG. 8, in an exemplary embodiment, the PharmARTS graphical user interface 600 may display a graphical navigation display request field 808 permitting the user to view a graphical representation. Selecting the graphical navigation display request field 808 may instruct the PharmARTS graphical user interface 600 to display a graphical navigation display to display the relations between the terms of the defining terms list and the candidate terms list. The user may navigate graphically through the graphical navigation display to refine the list of defining terms and/or candidate terms. Graphic navigation will be discussed in further detail below with reference to FIGS. 15-18. The method 1100 may continue to block 1104.

In block 1104, the method may include communicating data to cause display of the graphical navigation display at the computer. In an exemplary embodiment, the Directed Graph Language Writer Module 312 and/or the Graph Visualization Module 314 of the PharmARTS terminological server 206 may generate graphical user interface data to cause the computer 102 to generate the graphical navigation display.

Figure 12:
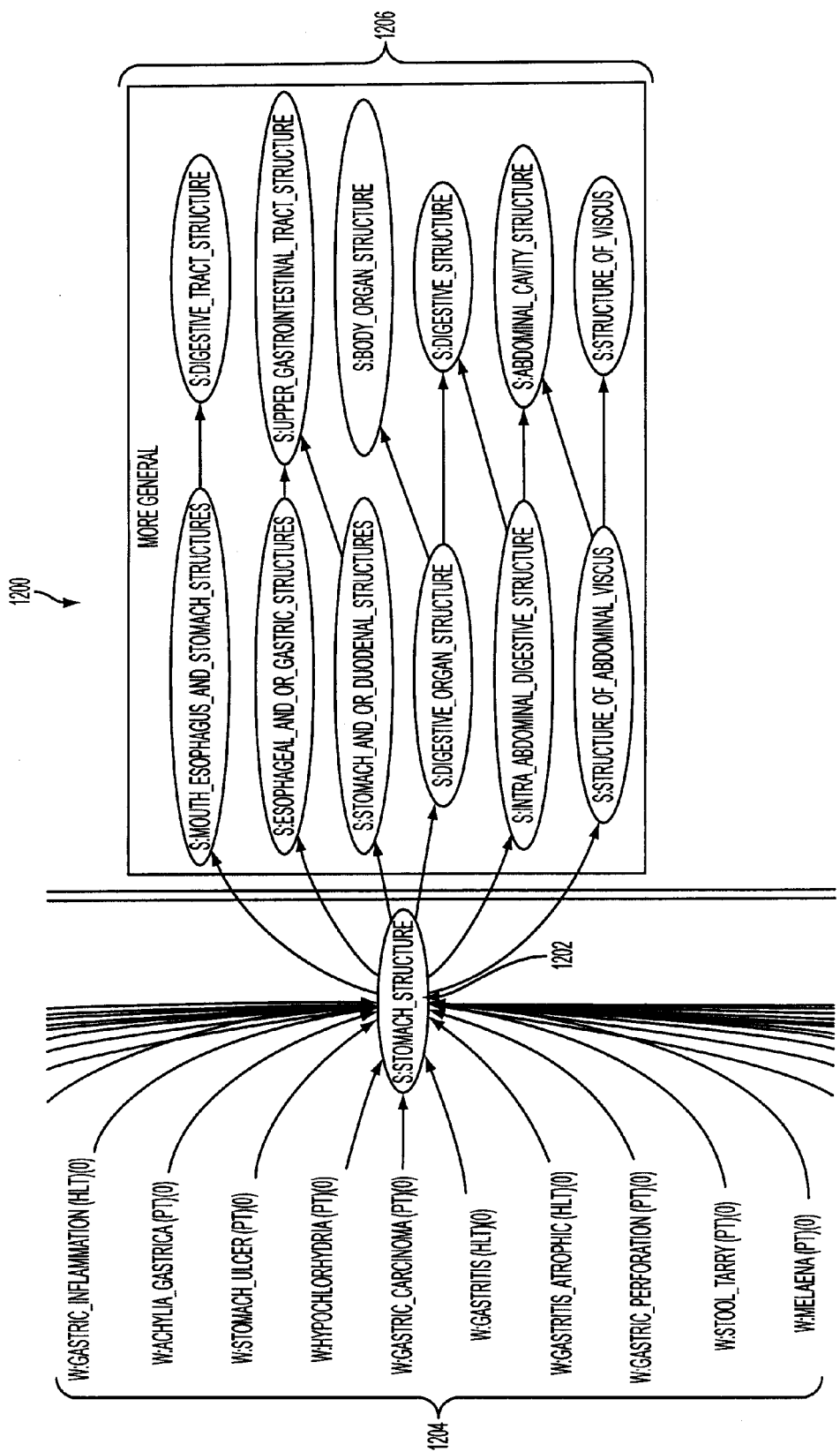
FIG. 12 illustrates a graphical navigation display in accordance with exemplary embodiments.

FIG. 12 illustrates a graphical navigation display in accordance with exemplary embodiments. The graphical navigation display 1200 may depict and organize all concepts as nodes connected to one or more central nodes 1202. Generally, a concept is a medical term which has been defined in the medical terminology (e.g., WHO-ART, MedDRA, etc.). An example of a concept is "gastric_carcinoma." The one or more central nodes 1202 may be one or more defining terms selected by the user from the defining term list display 706 in the PharmARTS graphical user interface 600 (see FIG. 8), which may be connected with other central nodes 1202 by logical relationships (e.g., AND/OR Boolean operators). The nodes depicted on the left of the central node 1202 in FIG. 12 are candidate nodes 1204 and the nodes depicted on the right of the central node 1202 are more general defining nodes 1206 that represent defining terms that are more general than the defining term of the central node 1202. The candidate nodes 1204 may be graphical representations of the candidate terms from the candidate term list field 804. The graphical navigation display 1200 also may represent the count of pharmacovigilance reports 1000 corresponding to each candidate node 1204, which may be activated by a user selecting a parameter (not shown) on the PharmARTS graphical user interface 600. In order to ensure confidentiality of the content of the pharmacovigilance database 106, this parameter is not activated in this figure and the count is represented as zero for each term in the list of candidate terms.

In the example depicted in FIG. 12, the user selected the SNOMED Stomach_structure defining term in the defining term list 706 of the PharmARTS graphical user interface 600 (see FIG. 8), and then selected the Graphic Navigation Display Request field 806 to instruct the PharmARTS system 104 to generate the graphical navigation display 1200. The graphical navigation display 1200 depicted in FIG. 12 includes the defining term Stomach_structure as the central node 1202, the candidate terms, which are graphically represented as candidate nodes 1204, from one or more controlled terminological structure that are related to diseases located in the stomach, and the more general defining terms, which are graphically represented as defining nodes 1206, that are more general than the Stomach_structure central node 1202 within the same terminological structure as the central node 1202. The graphical navigation display 1200 may permit the user to select a different central node 1202 by selecting one of the related candidate nodes 1204 and/or one of the more general defining nodes 1206 (see FIG. 11, block 1110). Once selected, the graphical navigation display 1200 may be updated to display the candidate nodes 1204 and the more general defining nodes 1206 associated with the different central node 1202. For example, the new central node may be a WHO-ART term node (see FIG. 11, block 1112), a SNOMED CT term node (see FIG. 11, block 1114), or a MedDRA term node (see FIG. 11, block 1116).

The candidate terms graphically represented as candidate nodes 1204 in the exemplary graphical navigation display 1200 depicted in FIG. 12 include candidate nodes 1204 graphically representing each of the WHO-ART terms gastric_inflammation (HLT), achylia_gastrica (PT), stomach_ulcer (PT), hypochlorhydria (PT), gastritis (HLT), gastritis_atrophic (HLT), gastric_perforation (PT), stool_tarry (PT), and melena (PT). Other candidate terms may be selected but are not drawn on FIG. 12. FIG. 12 illustrates a link between each of the candidate nodes 1204 and the central node 1202.

The defining terms graphically represented as defining nodes 1206 in the exemplary graphical navigation display 1200 include the SNOMED CT terms that are more general than the central node 1202 SNOMED CT term stomach_structure. FIG. 12 illustrates a link between the central node 1202 and each of the more general defining nodes 1206. In this example, the graphical display includes two levels of more general defining nodes, with the first level being narrower than the second level. One or more levels of more general defining nodes may be used. In the first level, the defining nodes 1206 include the terms mouth_esophagus_and_stomach_structures, esophageal_and_or_gastric_structures, stomach_and_or_duodenal_structures, digestive_organ_structure, intra_abdominal_digestive_structure, and structure_of_abdominal_viscus. In the second level, the defining nodes 1206 include the terms digestive_tract_structure, upper_gastro_intestinal_stract_structure, body_organ_structure, digestive_structure, abdominal_cavity_structure, and structure_of_viscus. The graphical navigation display 1200 also includes links between the first level and the second level to identify which terms in the second level relate to the terms in the first level. Moreover, the terms in the first level may be linked to one or more terms in the second level. For example, FIG. 12 depicts the defined node intra_abdominal_digestive_structure of the first level being linked to both the digestive_structure and the abdominal_cavity_structure in the second level. Hence, the more general defining terms digestive_structure and the abdominal_cavity_structure are broader than the more general defining term intra_abdominal-digestive_structure. It is noted that the graphical navigation display 1200 may include two or more central nodes 1202.

Figure 13:
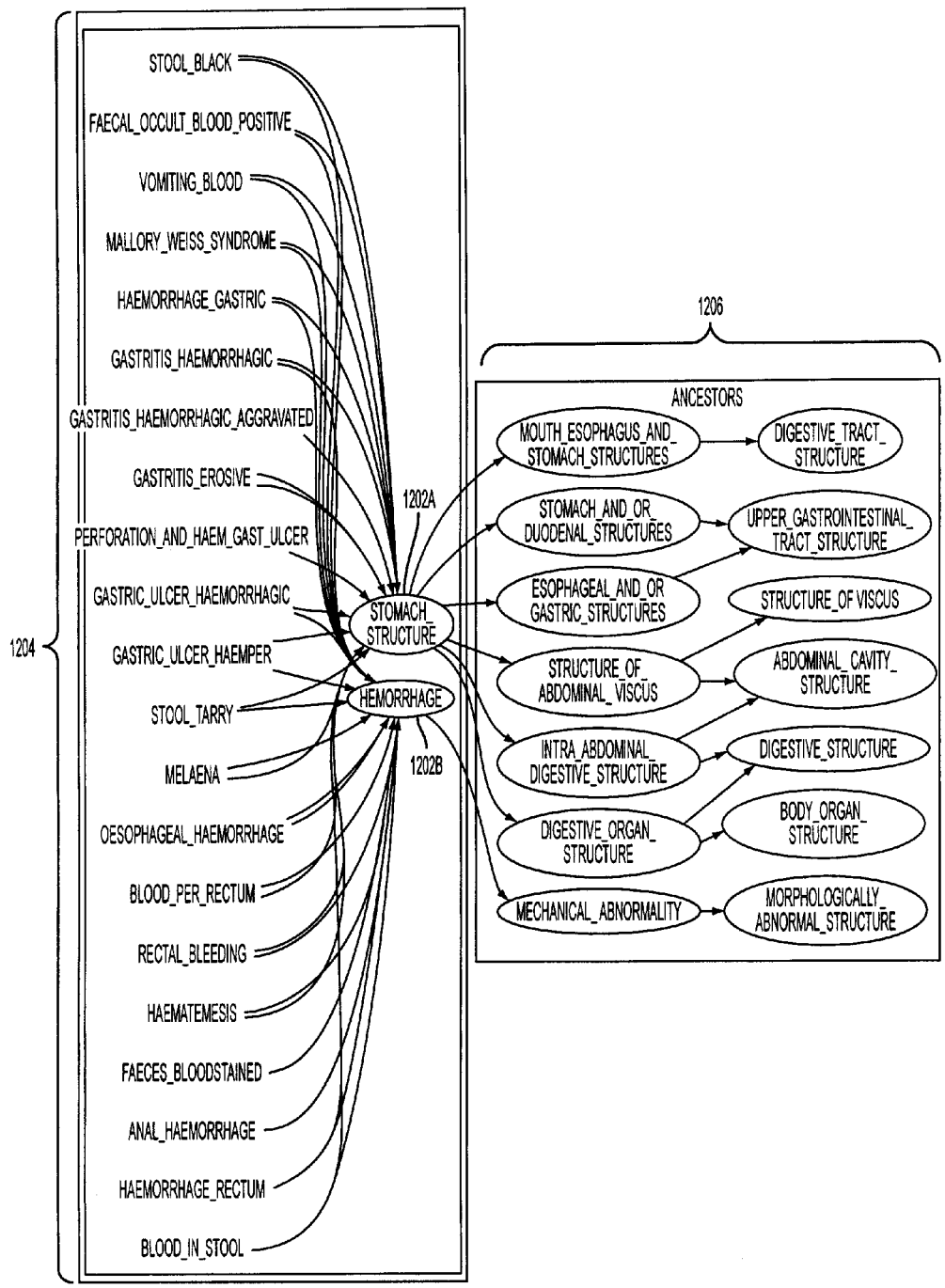
FIG. 13 illustrates a graphical navigation display illustrating a relationship between two central nodes in accordance with exemplary embodiments.

FIG. 13 illustrates a graphical navigation display illustrating a relationship between two central nodes in accordance with exemplary embodiments. The graphical navigation display 1200 includes two central nodes 1202A-B, the first central node 1202A representing the term stomach_structure and the second central node 1202B representing the term hemorrhage. The graphical navigation display 1200 displays a relationship between the two central nodes 1202A-B based on a Boolean AND operator, where candidate nodes 1204 are related to each of the central nodes 1202A-B. Each of the candidates nodes 1204 includes a link to both of the central nodes 1202A-B to represent that the candidate nodes 1204 are related to both of the central nodes 1202A-B. In another example, if the graphical navigation display 1200 displays a relationship between the two central nodes 1202A-B based on a Boolean OR operator, then the graphical navigation display 1200 would include a link to at least one the central nodes 1202A-B to represent that the candidate nodes 1204 are related to at least one the central nodes 1202A-B. Other relationships between the two central nodes 1202A-B also may be used. FIG. 13 also displays the more general defining terms in defining nodes 1206, similar to the more general defining nodes 1206 discussed above with respect to FIG. 12. By selecting one of the candidate node 1204, the PharmARTS terminological server 206 may update the graphical navigation display 1200 to graphically represent the relationships the selected candidate node 1204 has with more general defining nodes 1206.

Figure 14:
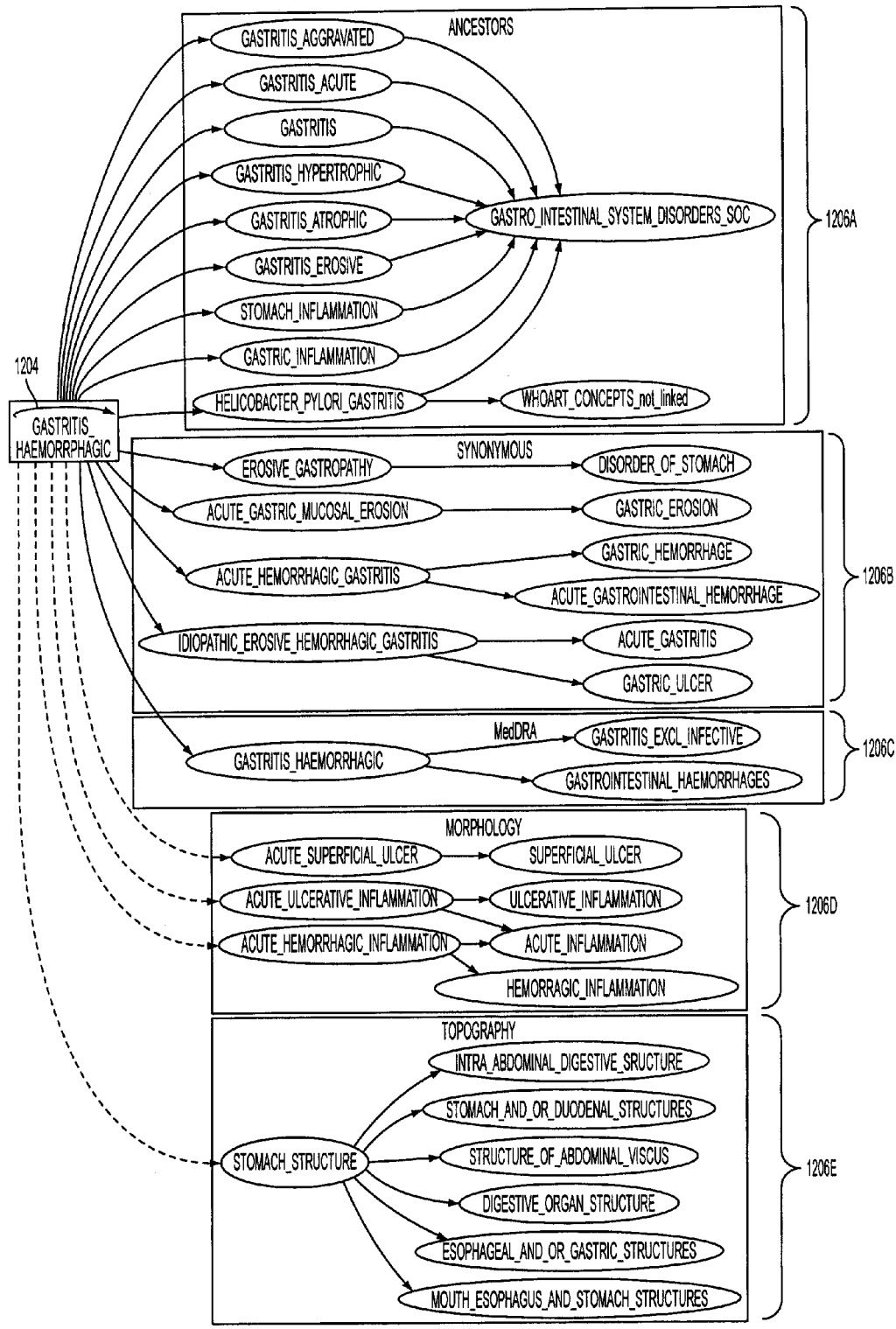
FIG. 14 depicts a graphical navigation display with a graphical representation of a relationship a selected candidate node has with one or more defining nodes in accordance with exemplary embodiments.

FIG. 14 depicts a graphical navigation display with a graphical representation of a relationship a selected candidate node has with one or more defining nodes in accordance with exemplary embodiments. In this example, the candidate node 1204 is related to five different sets of defining nodes: more general defining nodes 1206A, synonymous defining nodes 1206B, MedDRA defining nodes 1206C, morphology defining nodes 1206D, and topography defining nodes 1206E.

The more general defining nodes 1206A may represent a hierarchy of one or more levels of defining terms that are more general than the candidate term of the candidate node 1204. For example, the Gastritis_aggravated WHO-ART term is more general than the Gastritis_Haemorrhagic WHO-ART term. These relations between the WHO-ART terms are not necessarily part of the WHO-ART hierarchy and may be inferred by PharmARTS using terminological reasoning.

The synonymous defining nodes 1206B may identify defining terms within the terminology that are synonymous with the candidate term. For example, the candidate term gastritis_haemorrhagic in the WHO-ART terminology is synonymous with the defining term erosive_gastropathy in the WHO-ART terminology.

The MedDRA defining nodes 1206C may identify MedDRA terms synonymous with the candidate node 1204 in the MedDRA terminology. For example, the Gastritis_hemorrhagic WHO-ART term of the candidate node 1204 may be synonymous with the MedDRA term Gastritis_hemorrhagic of the MedDRA terminology.

The morphological defining nodes 1206D may identify defining concepts that are morphological characteristics of the candidate term identified by the candidate node 1204. Morphology is related to describing structural changes of the body. For example, the Gastritis_hemorrhagic WHO-ART term of the candidate node 1204 may have a morphological defining criteria for each of an Acute_superficial_ulcer defining term and an Acute_ulcerative_inflammation defining term. Generally, a defining criteria may be, for example, topography, morphology, function, and/or etiology of a medical condition. Other defining criteria also may be used, such as describing the evolution of the disease, severity of the disease, etc.

The topography defining node 1206E may identify defining concepts that are anatomical localizations of the candidate term identified by the candidate node 1204. Topogrpahy is related to describing detailed anatomic terms. For example, the Gastritis_hemorrhagic WHO-ART term of the candidate node 1204 may have a topographical defining criteria such as Stomach_structure.

It is noted that FIG. 14 is exemplary, and other relationships between the candidate terms and the defining terms may be graphically represented. For example, the graphical display may depict a relationship between candidate terms in a first terminology with terms in a second terminology. In another example, the graphical definition may display other kinds of defining criteria such as Function or Etiology, which are not displayed in FIG. 14 as they are not relevant in this example. Function may describe both normal and abnormal functions of the body. Etiology is the science that deals with the causes or origin of disease, and the factors which produce or predispose toward a certain disease or disorder. Etiology includes, for example, living agents such as, but not limited to, bacteria, viruses, or parasites.

The PharmARTS terminological server 206 also may be used to change a graph direction (see FIG. 11, block 1118) by either focalizing (see FIG. 11, block 1120) or generalizing (see FIG. 11, block 1122) the graphical navigation display 1200. Focalizing the graphical navigation display 1200 may be used to graphically display medical terms that are more specific than the central node 1202 within the same medical terminology. Generalizing the graphical navigation display 1200 may be used to graphically display medical terms that are more general than the central node 1202 within the same medical terminology.

Figure 15:
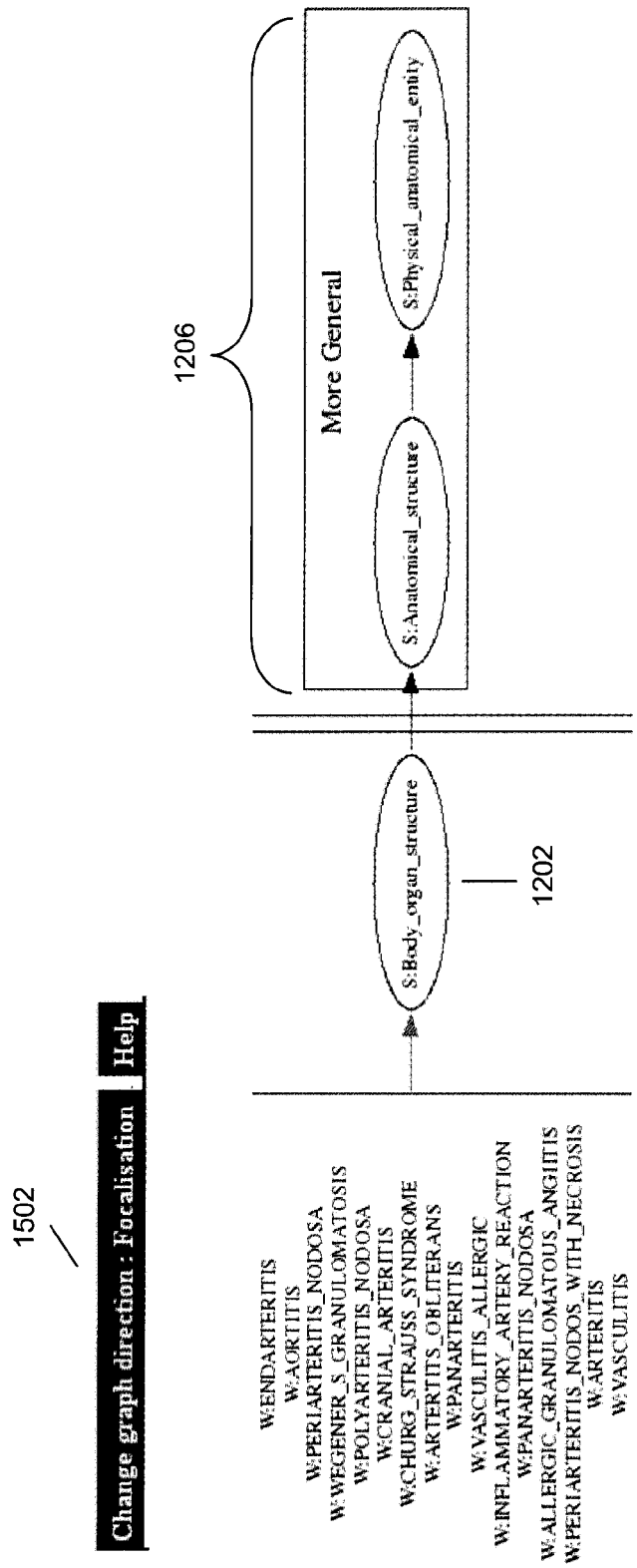
FIG. 15 illustrates focalizing a graphical navigation display in accordance with exemplary embodiments

FIG. 15 illustrates focalizing a graphical navigation display in accordance with exemplary embodiments. In this example, the central node 1202 is the SNOMED CT term Body_organ_structure. The graphical navigation display 1200 displays SNOMED CT terms that are more general than the SNOMED CT term Body_organ_structure. In this example, the graphical navigation display 1200 displays the more general defining nodes 1206 for the SNOMED CT term Anatomical_structure, followed by the even more general SNOMED CT term Physical_anatomical_entity. To reverse the direction of the graphical navigation display 1200 to display SNOMED CT terms that are more specific than the SNOMED CT term Body_organ_structure, the user may select the Change graph direction: Focalization field 1502.

Figure 16:
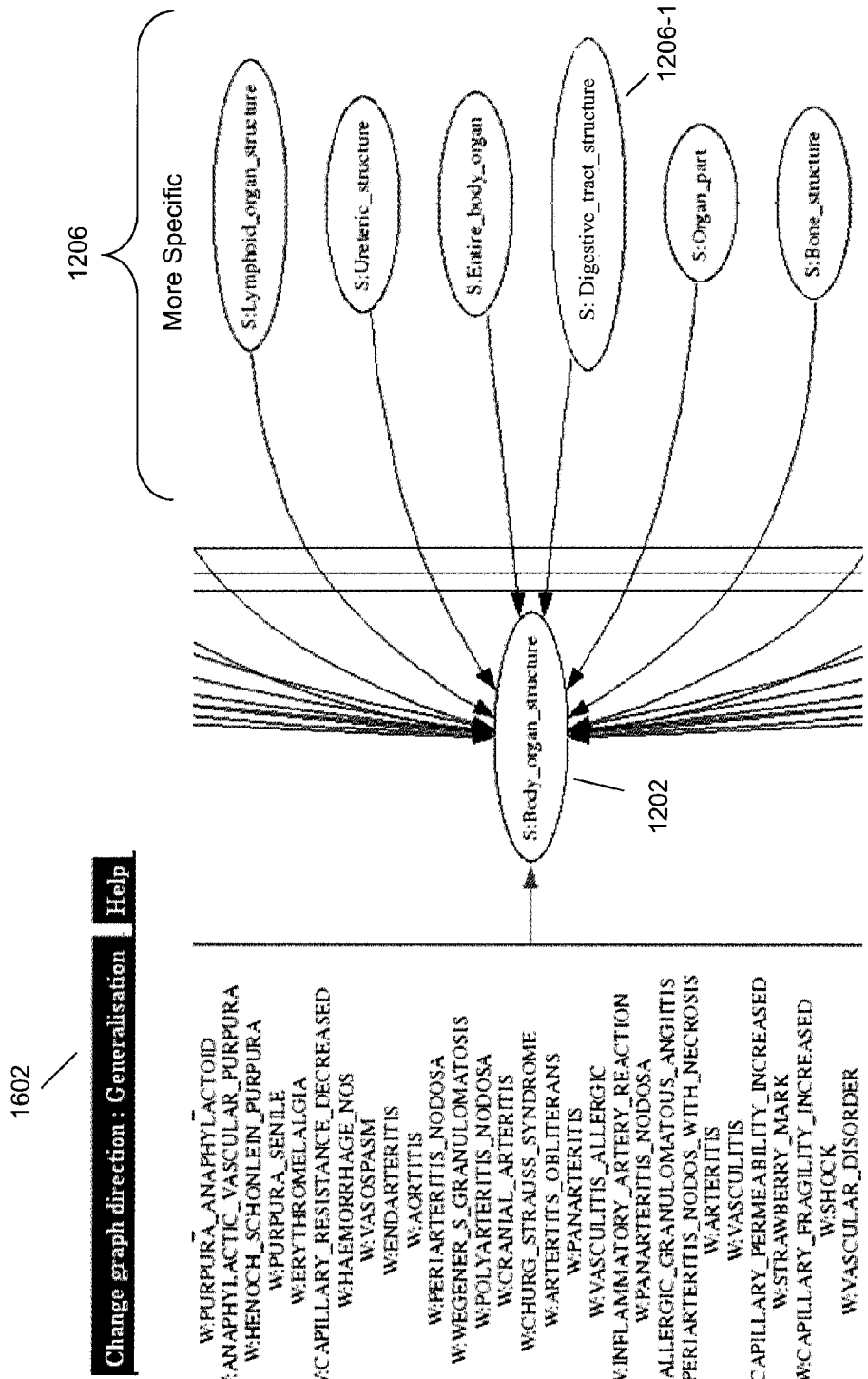
FIG. 16 illustrates a focalized graphical navigation display in accordance with exemplary embodiments.

FIG. 16 illustrates a focalized graphical navigation display in accordance with exemplary embodiments. FIG. 16 is the result of focalizing the graphical navigation display 1200 presented in FIG. 15. In FIG. 15, the central node 1202 is associated with the SNOMED CT term Body_organ_structure. The focalized graphical navigation display 1200 depicts the more specific nodes 1606 related to the SNOMED CT term body_organ_structure. In this example, the more specific nodes include the defining terms Lymphoid_organ_structure, ureteric_structure, entire_body_organ, etc. The user may select the Change graph direction: Generalization field 1602 to reverse the direction of the graphical navigation display 1200 to return to FIG. 15. The user also may select one of the more specific defining nodes 1206 to change the central node 1202. For example, the use may select the more specific digestive_tract_structure more general defining node 1206-1 to make this node the new central node 1202.

Figure 17:
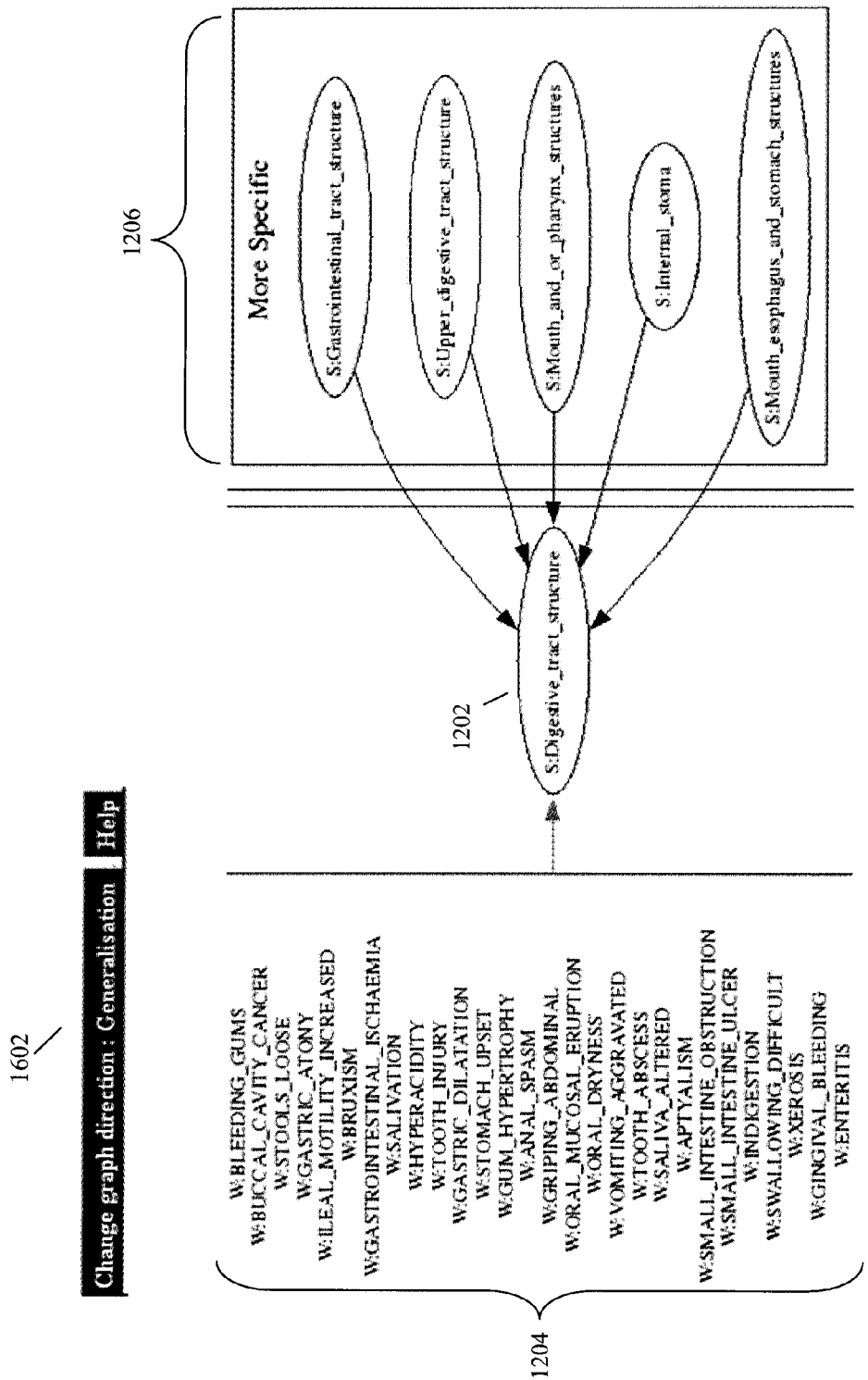
FIG. 17 illustrates a graphical navigation display after selection of a new central node in accordance with exemplary embodiments.

FIG. 17 illustrates a graphical navigation display after selection of a new central node in accordance with exemplary embodiments. In this example, selecting the more specific defining digestive_tract_structure defining node 1206-1 instructs the PharmARTS terminological server 206 to update the graphical navigation display 1200 to depict the digestive_tract_structure defining node as the central node 1202. The updated graphical navigation display 1200 graphically displays to the user which kinds of structures are present in the digestive tract to refine his or her analysis. In this example, the defining nodes 1206 that are more specific than the central node 1202 term of digestive_tract_structure are the defining terms from SNOMED CT including gastro_intestinal_tract_structure, upper_digestive_tract_structure, mouth_and_pharynx_structures, internal_stoma, and mouth_esophagus_and_stomach_structures. The user also may select the Change graph direction: Focalization field 1602 to show the terms that are more general than the digestive_tract_structure central node 1202, similar to the discussion provided with respect to FIGS. 15-16.

The PharmARTS system 104 provides numerous advantages over conventional systems, several of which are discussed below. The PharmARTS system 104 assists in efficient retrieval of pharmacovigilance reports 1000. In one use scenario, a pharmacovigilance specialist may need to know if a drug is related to a given medical condition. The specialist may access the PharmARTS system 104 to search for a set of pharmacovigilance reports 1000 that describe any adverse drug reactions associated with the given medical condition. The medical condition may be represented as a single term in a controlled terminology (e.g., WHO-ART or MedDRA) or as a set of terms in one or more controlled terminologies.

A challenge in accessing pharmacovigilance reports 1000 is that the number of the pharmacovigilance reports 1000 related to adverse drug reactions are increasing exponentially. It is difficult to hire enough physicians and pharmacists in pharmacovigilance units of pharmaceutical companies. An increased number of pharmacovigilance staff are scientists without sufficient medical skills to perform optimal search in pharmacovigilance databases. In conventional systems, the pharmacovigilance specialist would be required to have a good knowledge of the controlled terminologies (e.g., WHO-ART or MedDRA) that are used to code adverse drug reactions in pharmacovigilance databases 106. A good knowledge of controlled terminologies requires training that may be costly and experience that may take a long time to develop, especially for large terminologies, such as MedDRA. Indeed, MedDRA contains more than fifty thousand low level terms (LLT). The large number of MedDRA terms may make it difficult to identify the high level categories (e.g., SOC: System Organ/Class, HLGT: High Level Group Term, and HLT: High level Term) to which a LLT belongs. Moreover, a medical condition may be described by a set of terms that belong to different high level categories in MedDRA. Additionally, a high level category may contain terms that are relevant for describing the given medical condition and other terms that are not relevant. Therefore, PharmARTS system 104 may be used to filter the high level categories to improve search accuracy.

The PharmARTS system 104 also presents an additional layer that allows access to pharmacovigilance data in a simple and intuitive way. The PharmARTS system 104 may be used to improve search quality even if queries are performed by pharmacovigilance staff having little skills related to MedDRA and a limited knowledge of medicine. The PharmARTS system 104 may be used to provide faster and more exhaustive searching of pharmacovigilance databases 106. This leads to the user being able to process more pharmacovigilance reports 1000 without increasing the number of people required to process the pharmacovigilance data. Moreover, the user does not need to have extensive knowledge of the controlled medical terminologies. The user may describe the medical condition according to defining criteria that are sound for a health professional. The defining criteria may be, for example, topography, morphology, function, and etiology of the medical condition. Other defining criteria also may be used, such as describing the evolution of the disease, severity of the disease. etc.

One way this advantage is achieved is by the PharmARTS system's 104 linking of the WHO-ART/MedDRA terms with a formal definition in SNOMED-CT. When the user queries for a set of medical terms, PharmARTS system 104 may identify the set of WHO-ART/MedDRA terms that share the same defining criteria with the given medical condition.

The PharmARTS system 104 also advantageously provides a graphical user interface that allows browsing the WHO-ART/MedDRA terminologies through a graphical representation of formal definitions of terms using a categorical structure. As such, graphical browsing of the controlled terminologies is not constrained by high level categories already present in these medical terminologies. Instead, refining of the query may occur graphically by browsing the hierarchies within categorical structure of medical terminologies provided in the graphical navigation display 1200.

Another advantage the PharmARTS system 104 provides is in assisting a user in coding a pharmacovigilance report 1000. A health professional (e.g., physician, pharmacist, dentist, nurse . . . ) may send a spontaneous report describing an adverse drug reaction to a pharmacovigilance national center or a pharmacovigilance unit in a pharmaceutical company.

The report may include a verbatim, which is a natural language expression used by the health professional to describe the adverse drug reaction. The label of the verbatim often does not correspond to terms belonging to a controlled medical terminology. The PharmARTS system 104 may permit the user to find a medical term in a controlled medical terminology (e.g., WHO-ART or MedDRA) that most appropriately describes the verbatim.

In conventional systems, finding one or more terms belonging to vocabulary of a controlled terminology based on the verbatim is difficult as conventional systems are based on lexical approaches. Lexical approaches provide assistance for coding on a comparison of lexical patterns between the verbatim and terms from a controlled terminology. Terms which share the same meaning, however, may have different lexical patterns. In order to search a code at the conceptual level, browsers are restricted to high level categories already present in the controlled terminology. As terms may belong to different high level categories, however, this may inefficiently require the user to have to identify every high level category where the term may belong and browse through each of these high level categories.

The PharmARTS system 104 also may be used to improve coding at the conceptual level. Unlike conventional systems, the PharmARTS system 104 permits the user to describe the term he or she is looking for as a set of defining criteria. The PharmARTS system 104 may then match the definition (defining criteria) of the term for which the user is looking with definitions (defining criteria) of terms from one or more controlled terminologies. To do this, the PharmARTS system 104 may provide a graphical user interface that allows browsing of the WHO-ART/MedDRA terminologies through a graphical representation of formal definitions of terms using a categorical structure provided in the graphical navigation display 1200. Therefore, graphical browsing of the controlled terminologies is not constrained by high level categories already present in these controlled terminologies. As such, the query may be graphically refined as the user browses the hierarchies of nodes from the categorical structure presented in the graphical navigation display.

The PharmARTS system 104 also may facilitate a user in building a customized set of terms. Terms which describe a given medical condition in a controlled terminology (e.g., WHO-ART or MedDRA) are often located in different high level categories, for example, terms may be in different system organ/classes. Therefore, it is not possible in conventional systems to perform queries according to a single high level category. One conventional solution is to build a custom set of terms that describe the given medical condition. This set of terms can be used on different pharmacovigilance databases at different times. For example, the MedDRA Maintenance Support and Services Organization (MSSO) provides several Standard MedDRA Queries (SMQs) to achieve this objective.

Controlled medical terminologies for pharmacovigilance, however, are large and candidate terms for the SMQ belong to several high level categories. Browsing the WHO-ART or MedDRA terminologies is a manual task that requires significant training and experience. Building customized sets of terms requires a long time because the user needs to identify every high level category that is relevant for the customized set of terms. And in each high level category, the user has to select the relevant terms for the customized set of terms.

The PharmARTS system 104, however, does not require the user to identify and browse every high level category of the controlled terminology that is a candidate for providing terms for the customized set of terms. Instead, the user may define the customized set of terms as a set of defining criteria with logical relationships (e.g., Boolean operators) between defining criteria. The PharmARTS system 104 may then retrieve every term from the one or more controlled medical terminologies that match the defining criteria, regardless of where the terms may be classified in each high level category. The PharmARTS system 104 may provide a PharmARTS graphical user interface that allows browsing the WHO-ART/MedDRA terminologies through a graphical representation of formal definitions of terms using a categorical structure presented in the graphical navigation display. Therefore, graphical browsing of the controlled terminologies is not constrained by high level categories already present in these terminologies. The query may be graphically refined by browsing the hierarchies of nodes within the categorical structure presented in the graphical navigation display.

Thus, the PharmARTS system may provide innovative functionalities to assist individuals responsible for analysis and coding of pharmacovigilance reports in regulatory authorities, pharmacovigilance centers, or pharmaceutical companies. The PharmARTS system may address issues related to current limits of conventional terminologies used for coding adverse drug reactions in pharmacovigilance databases.

The PharmARTS system may assist the user in: case retrieval (e.g., the user wishes to obtain drug safety reports related to a specific medical condition); coding of pharmacovigilance reports (e.g., the user wishes to obtain the most appropriate coding term for a specific drug safety case and navigates through different contexts of related terms); and building a customized set of terms (e.g., the user wishes to build a set of terms that represent a medical condition and use this set of terms in future analyses of his pharmacovigilance dataset).

The PharmARTS system in accordance with exemplary embodiments makes it possible to carry out a research on multiple different medical terminologies (e.g., SNOMED CT, WHO-ART, and MedDRA) starting from a string or a substring. The research in these different medical terminologies may allow retrieving pharmacovigilance reports related to a medical term selected by the user that corresponds to the string or substring.

The PharmARTS system also may allow a graphic visualization of the definition of a selected medical term and may permit a user to navigate through different contexts of related terms in a same or different terminology. Navigation through the semantic context in the graphical mode also may help the user to choose the most appropriate term corresponding to the description of the drug safety report and therefore assist coding procedure. The PharmARTS system may be implemented in a web environment, allowing collaborative work for case coding and case retrieval, where several users can simultaneously use the PharmARTS terminological server.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

The invention claimed is:

1. A method for browsing a pharmacovigilance database with a graphical representation that shows relationships between medical terms comprising:
   providing access to a plurality of medical terminologies comprising at least a first controlled medical terminology and a second controlled medical, adverse-event terminology, wherein each of the plurality of controlled medical terminologies comprises a plurality of controlled medical terms;
   mapping the medical terms of the plurality of controlled medical terminologies to a searchable database by using a semantic network to relate the medical terms of the different controlled medical terminologies, wherein the mapping using the semantic network creates an inferred hierarchy for the second controlled medical, adverse-event terminology based on a hierarchy of the first controlled medical terminology; and
   providing a graphical user interface that enables graphical navigation of the plurality of controlled medical terminologies, enables display of a mapping between a first medical term from the first controlled medical terminology to a second medical term from the second controlled medical, adverse-event terminology, and enables coding of pharmacovigilance reports using medical terms of the second controlled medical, adverse-event terminology based on a formal definition provided using medical terms of the first controlled medical terminology, wherein the second controlled medical, adverse-event terminology is a Medical Dictionary for Regulatory Activities.

2. The method of claim 1, further comprising receiving a query request to search the plurality of controlled medical terminologies on a medical issue, wherein the query comprises:
   one or more of a morphology relationship, a functional relationship, an etiology relationship and a topography relationship between the first controlled medical term from a first controlled medical, terminology and a second controlled medical term from the second controlled medical, adverse-event terminology;
one or more defining terms wherein defining terms are controlled medical terms from a plurality of controlled medical terminologies; and
a plurality of operators to express relations between the defining terms.

3. The method of claim 2, further comprising causing display of a graphical navigation display, the graphical navigation display being useable to display a plurality of concept nodes and relationships between the plurality of concept nodes.

4. The method of claim 3, wherein the relationships identify one or more of a morphology relationship, an ancestry relationship, a functional relationship, a synonymous term relationship within a terminology, an etiology relationship, a topography relationship, and an alternative synonymous term relationship between the first medical term from the first controlled medical terminology and the second controlled medical term from the second controlled medical, adverse-event terminology.

5. The method of claim 3, further comprising receiving an input to graphically navigate in the graphical navigation display, wherein the graphical navigation modifies the query by replacing the defining term by the defining term selected in the display.

6. The method of claim 5, wherein the graphical navigation displays a set of second adverse event medical terms linked through a relationship to two or more medical terms from the first controlled medical terminology, wherein the relationship is a union or an intersection relationship within the query.

7. The method of claim 1, wherein the semantic network is a Unified Medical Language System.

8. The method of claim 1, wherein the first controlled medical terminology is a Systematized Nomenclature of Medicine Clinical terms terminology.

9. The method of claim 3, further comprising receiving a focalization request to request that the graphical navigation display identify medical terms that are more specific than the first medical term, wherein the display replaces at least one parent-node and corresponding relationships with at least one child-node and corresponding relationships.

10. The method of claim 3, further comprising receiving a generalization request to request that the graphical navigation display identify medical terms that are less specific than the first medical term, wherein the display replaces at least one child-node and corresponding relationships with at least one parent-node and corresponding relationships.

11. The method of claim 1, further comprising receiving a search request, the search request comprising a selection of at least one of the plurality of controlled medical terminologies and a search string.

12. The method of claim 11, further comprising searching the searchable database based on the search string to identify a list of defining terms, the list of defining terms identifying one or more defining terms from at least one of the plurality of controlled medical terminologies.

13. The method of claim 12, wherein the list of defining terms comprises at least one defining term that contains the search string.

14. The method of claim 13, further comprising:
receiving a term selection request that selects the defining term;
generating a query wherein the query comprises one or more of: a morphology relationship, a functional relationship, an etiology relationship and a topography relationship between a first controlled medical term from the first controlled medical, terminology and a second controlled medical term from the second controlled medical, adverse-event terminology; and the selected defining term; and
generating a list of candidate terms related to the defining term using the generated query, wherein the list of candidate terms includes one or more candidate terms having one or more of: a morphology relationship, a functional relationship, an etiology relationship, and a topography relationship with the defining term identified by the semantic network.

15. The method of claim 13, further comprising:
receiving a term selection request that selects a first defining term and a second defining term and identifies a logical relationship between the first defining term and the second defining term;
generating a query comprising:
one or more of a morphology relationship, a functional relationship, and a topography relationship between the first medical term from a first controlled medical, terminology and a second controlled medical term from the second controlled medical, adverse-event terminology;
two defining terms wherein defining terms are controlled medical terms from a plurality of controlled medical terminologies; and
a plurality of operators to express relationships between the defining terms; and
generating a list of candidate terms related to the defining terms using the generated query, wherein the list of candidate terms includes one or more candidate terms having a relationship with the defining terms identified by the semantic network.

16. The method of claim 15, wherein the operator expressing the logical relationship is a theory operator between a first list of candidate terms related to the first defining term and a second list of candidate terms related to the second defining term in the query.

17. The method of claim 15, further comprising receiving a clear restriction request that removes the logical relationship in the query wherein the logical relationship comprises a defining term and its associated operator.

18. A non-transitory computer readable media comprising code to perform the acts of the method of claim 1.

19. A system for browsing a pharmacovigilance database with a graphical representation that shows relationships between medical terms comprising:
a resource server database comprising a plurality of controlled medical terminologies, wherein the plurality of controlled medical terminologies comprises at least a first controlled medical terminology and a second controlled medical, adverse-event terminology and a semantic network that expresses relations between medical terms of the plurality of controlled medical terminologies, wherein each of the plurality of controlled medical terminologies comprises a plurality of controlled medical terms;
a terminology server having at least one programmed computer processor that maps the medical terms of the plurality of controlled medical terminologies to a searchable database by using the semantic network to relate the medical terms of the different controlled medical terminologies, wherein the mapping using the semantic network creates an inferred hierarchy for the second controlled medical, adverse-event terminology based on a hierarchy of the first controlled medical terminology, and wherein the terminology server providing a graphical user interface that enables graphical navigation of the plurality of controlled medical terminologies, enables display of a mapping between a first medical term from the first controlled medical terminology to a second medical term from the second controlled medical, adverse-event terminology, and enables coding of pharmacovigilance reports using medical terms of the second controlled medical, adverse-event terminology based on a formal definition provided using medical terms of the first controlled medical terminology, wherein the second controlled medical, adverse-event terminology is a Medical Dictionary for Regulatory Activities.

20. A system comprising at least one programmed computer processor for browsing a pharmacovigilance database with a graphical representation that shows relationships between medical terms comprising:

means for providing access to a plurality of controlled medical terminologies comprising at least a first controlled medical terminology and a second controlled medical, adverse-event terminology, wherein each of the plurality of controlled medical terminologies comprises a plurality of controlled medical terms;

means for mapping the medical terms of the plurality of controlled medical terminologies to a searchable database by using a semantic network to relate the medical terms of the different controlled medical terminologies, wherein the mapping using the semantic network creates an inferred hierarchy for the second controlled medical, adverse-event terminology based on a hierarchy of the first controlled medical terminology; and means for providing a graphical user interface that enables graphical navigation of the plurality of controlled medical terminologies, enables display of a mapping between a first medical term from the first controlled medical terminology to a second controlled medical term from the second controlled medical, adverse-event terminology, and enables coding of pharmacovigilance reports using controlled medical terms of the second controlled medical, adverse-event terminology based on a formal definition provided using medical terms of the first controlled medical terminology, wherein the second controlled medical, adverse-event terminology is a Medical Dictionary for Regulatory Activities.

* * * * *